US006811988B2

(12) United States Patent
Chojkier et al.

(10) Patent No.: US 6,811,988 B2
(45) Date of Patent: Nov. 2, 2004

(54) COMPOSITIONS AND METHODS FOR DIAGNOSING ALZHEIMER'S DISEASE

(76) Inventors: Mario Chojkier, 12531 El Camino Real, San Diego, CA (US) 92130; Martina Buck, 4070 Huerfano Ave., #128, San Diego, CA (US) 92117

(*) Notice: Subject to any disclaimer, the term of this patent is extended or adjusted under 35 U.S.C. 154(b) by 54 days.

(21) Appl. No.: 10/278,181

(22) Filed: Oct. 21, 2002

(65) Prior Publication Data

US 2003/0104488 A1 Jun. 5, 2003

Related U.S. Application Data

(62) Division of application No. 09/731,460, filed on Dec. 7, 2000, now Pat. No. 6,495,335.

(51) Int. Cl.$^7$ .............................................. C12P 19/00
(52) U.S. Cl. ................... 435/7.2; 436/503; 424/130.1; 424/178.1; 530/300; 530/402
(58) Field of Search ......................... 435/7.2; 436/503; 424/130.1, 178.1; 530/300, 402

(56) References Cited

U.S. PATENT DOCUMENTS

| | | | |
|---|---|---|---|
| 4,816,388 A | 3/1989 | Sipe et al. | |
| 5,508,167 A | 4/1996 | Roses et al. | |
| 5,580,748 A | 12/1996 | Alkon et al. | |
| 5,716,828 A | 2/1998 | Roses et al. | |
| 5,767,248 A | 6/1998 | Roses et al. | |
| 5,958,919 A | 9/1999 | Olney et al. | |
| 5,986,054 A | 11/1999 | St. George-Hyslop et al. | |
| 6,010,874 A | 1/2000 | Hardy | |
| 6,027,896 A | 2/2000 | Roses et al. | |
| 6,027,899 A | 2/2000 | Lehmann et al. | |
| 6,495,335 B2 * | 12/2002 | Chojkier et al. | ............ 435/7.92 |

FOREIGN PATENT DOCUMENTS

WO   WO 98/12561   3/1998

OTHER PUBLICATIONS

Bermejo et al., Gerontology, 1997; 43:218–222.*
Anderson et al., "Exact cleavage site of Alzheimer amyloid precursor in neuronal PC–12 cells," Neurosci. Lett., 128:126–128 (1991).
Ausubel et al. (eds.), Current Protocols in Molecular Biology, Ch. 11, "Immunology," John Wiley & Sons, Inc., New York (1994).
Behl et al., "Vitamin E Protects Nerve Cells from Amyloid β Protein Toxicity," Biochem. Biophys. Res. Commun., 186:944–950 (1992).
Borden et al., "Resting $[Ca^{2+}]_i$ and $[Ca^{2+}]_i$ Transients Are Similar in Fibroblasts From Normal and Alzheimer's Donors," Neurobiol. of Aging 13:33 [1991].
Chartier–Harlin et al., "Early–onset Alzheimer's disease caused by mutations at codon 717 of the β–amyloid precursors protein gene," Nature 353:844–846 [1991].
Cole et al., "The EBV–Hybridoma Technique and Its Application to Human Lung Cancer," in Monoclonal Antibodies and Cancer Therapy, Alan R. Liss, Inc., pp. 77–96 [1985].

Copani et al., "Activation of Metabotropic Glutamate Receptors Protects Cultured Neurons Against Apoptosis Induced by β–Amyloid Peptide," Molecular Pharmacology 47:890–897 [1995].
Coyle et al., "Oxidative Stress, Glutamate, and Neurodegenerative Disorders," Science 262:689–695 [1993].
Crowther, "Enzyme–Linked Immunosorbent Assay (ELISA)," in Molecular Biomethods Handbook, Rapley et al. [eds.], pp. 595–617, Humana Press, Inc., Totowa, NJ [1998].
Glenner et al., "Alzheimer's Disease: Initial Report of the Purification and Characterization of a Novel Cerebrovascular Amyloid Protein," Biochem. Biophys. Res. Commun., 120:885–890 [1984].
Haass and Selkoe, "Cellular processing of β–Amyloid Precursor Protein and the Genesis of Amyloid β–Peptide," Cell 75:1039–1042 [1993].
Haass et al., "Amyloid β–peptide is produced by cultured cells during normal metabolism," Nature 359:322–324 [1992].
Harlow and Lane (eds.), Antibodies: A Laboratory Manual, Cold Spring Harbor Laboratory Press [1988].
Healey et al., "A rapid semi quantitative capillary enzyme immunoassay for digoxin," Clin. Chim. Acta 134:51–58 [1983].
Jeanson et al., "Comparison of conjugation procedures for the preparation of monoclonal antibody–enzyme conjugates," Immunol. Methods 111:261–270 [1988].
Kennedy et al., "Familial Alzheimer's disease," Brain 116:3009–324 [1993].
Kohler and Milstein, "Continuous cultures of fused cells secreting antibody of predefined specificity," Nature 256:495–497 [1975].
Kosik, "Alzheimer's Disease: A Cell Biological Perspective," Science 256:780 [1992].
Kozbor et al., "The production of monoclonal antibodies from human lymphocytes," Immunol. Today 4:72 [1983].
Laurino et al., "Monoclonal Antibodies, Antigens and Molecular Diagnostics: A Practical Overview," Ann. Clin. Lab Sci., 29(3):158–166 [1999].
Le et al., "Cell death induced by β–amyloid 1–40 in MES 23.5 hybrid clone: the role of nitric oxide and NMDA–gated channel activation leading to apoptosis," Brain Res., 686:49–60 [1995].

(List continued on next page.)

Primary Examiner—Sharon Turner
(74) Attorney, Agent, or Firm—Medlen & Carroll, LLP (57) ABSTRACT

The present invention provides methods and compositions for the diagnosis of Alzheimer's disease. In particular, the present invention provides modified beta-amyloid peptides, antibodies that specifically bind to the modified beta-amyloid peptides, and methods for using these compositions in the diagnosis of Alzheimer's disease, as well as methods to monitor treatment and/or disease progression of Alzheimer's disease in patients. The present invention also provides compositions and methods useful in research involving amyloid precursor protein (APP) metabolism and Alzheimer's disease.

11 Claims, 1 Drawing Sheet

OTHER PUBLICATIONS

Mark et al., "Amyloid β–Peptide Impairs Ion–Motive ATPase Activities: Evidence for a Role in Loss of Neuronal $Ca^{2+}$Homeostasis and Cell Death," *J. Neurosci.*, 15:6239–6249 [1995].

Mattson et al., "β–Amyloid precursor protein metabolities and loss of neuronal $Ca^{2+}$homeostasis in Alzheimer's disease," *Trends Neurosci.*, 16:409–414 [1993].

Mattson et al., "β–Amyloid Peptides Destabilize Calcium Homeostasis and Render Human Cortical Neurons Vulnerable to Excitotoxicty," *Neuroscience* 12:376 [1992].

Nakane and Kawaoi, "Peroxidase–Labeled Antibody, A New Method of Conjugation," *J. Histochem. Cytochem.*, 22:1084–1091 [1988].

Pappolla et al., in "Perspectives in behavioral medicine, Alzheimer's disease and AIDS," Stein et al. [eds.], Academic Press, San Diego, California, pp. 3–20 [1995].

Pappolla et al., "The Heat Shock/Oxidative Stress Connection," *Mol. Chem. Neuropathol.*, 28:21–34 [1996].

Perl and Brody, "Alzheimer's Disease: X–ray Spectrometric Evidence of Aluminum Accumulation in Neurofibrillary Tangle–Bearing Neurons," *Science* 208:297 [1980].

Perl, "Relationship of Aluminum to Alzheimer's Disease," *Environmental Health Perspective* 63:149 [1985].

Peterson et al., "Altered Response of Fibroblasts From Aged and Alzheimer Donors to Drugs That Elevate Cytosolic Free Calcium," *Neurobiology of Aging* 9:261 [1988].

Robakis et al., "Involvement of Amyloid as a Central Step in the Development of Alzheimer's Disease," *Neurobiol. Aging* 15:S127–129 [1994].

Robakis et al., "Molecular cloning and characterization of a cDNA encoding the cerebrovascular and the neuritic plaque amyloid peptides," *Proc. Natl. Acad. Sci. USA* 84:4190–4194 [1987].

Sambrook et al. (eds.), Molecular Cloning, Cold Spring Harbor Laboratory Press [1989].

Shoji et al., "Production of the Alzheimer Amyloid β Protein by Normal Proteolytic Processing," *Science* 258:126–129 [1992].

Teller et al., "Presence of soluble amyloid β–peptide precedes amyloid plaque formation in Down's syndrome," *Nature Med.*, 2:93 [1996].

Voller et al., "Enzyme immunoassays in diagnostic medicine, Theory and Practice," *Bull. W.H.O.*, 53:55–65 [1976].

Weidemann et al., "Identification, Biogenesis, and Localization of Precursors of Alzheimer's Disease A4 Amyloid Protein," *Cell* 57:115–126 [1989].

Yankner et al., "Neurotrophic and Neurotoxic Effects of Amyloid β Protein: Reversal by Tachykinin Neuropeptides," *Science* 250:279–282 [1990].

Buck et al., "Muscle wasting and dedifferentiation induced by oxidative stress in a murine model of cachexiz is prevented by inhibitors of nitric oxide synthesis and antioxidants," *EMBO J.*, 15:1753–1765 [1996].

Buck et al., "Phosphorylation of Rat Serine 105 or Mouse Threonine 217 in C/EBPβ Is Required for Hepatocyte Proliferation Induced by TGFa," *Molecular Cell* 4:1087–1092 [1999].

Harrington and Colaco, "A glycation connection," *Nature* 370:247–248 [1994].

Smith et al., "Advanced Maillard reaction end products are associated with Alzheimer disease pathology," *Proc. Natl. Acad. Sci. USA* 91:5710–5714 [1994].

Vitek et al., "Advanced glycation end products contribute to amyloidosis in Alzheimer disease," *Proc. Natl. Acad. Sci. USA* 91:4766–4770 [1994].

Yan et al., "Glycated tau potein in Alzheimer disease: A mechanism for induction of oxidant stress," *Proc. Natl. Acad. Sci. USA* 91:7787–7791 [1994].

Hall et al., "Immunocytochemical method for investigating in vivo neuronal oxygen radical–induced lipid peroxidation," *Journal of Neuroscience Methods*, 76: 115–112 [1997].

Horie–et al., "Immunohistochemical colocalization of glycoxidation products and lipid peroxidation products in diabetic renal glomerular lesions," *Journal of Clinical Investigation*, 100:2995–3004 [1997].

Oostveen et al., "Neuroprotective efficacy and mechanisms of novel pyrrolopyrimidine lipid peroxidation inhibitors in the gerbil forebrain ischemia Model," *Journal of Cerebal Blood Flow and Metabolism*, 18:539–547 [1998].

Palainski et al., "Antisera and monoclonal antibodies specific for epitopes generated during oxidative modification of low density lipoprotein," *Arteriosclerosis*, 10:325–335 [1990].

Yan et al., "Role of ERAB/L–3–hydroxyacyl–coenzyme A dehydrogenase type II activity in Aβ–induced cytoxicity," *Journal of Biological Chemistry*, 274:2145–2156 [1999].

* cited by examiner

FIGURE 1

SEQUENCE LISTING

```
<160> NUMBER OF SEQ ID NOS: 1

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence:  Synthetic

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

COMPOSITIONS AND METHODS FOR DIAGNOSING ALZHEIMER'S DISEASE

This Application is a Divisional of U.S. patent appln. Ser. No. 09/731,460, filed Dec. 7, 2000 now U.S. Pat. No. 6,495,335.

This invention was made during the course of work supported in part by the United States Government, under the National Institutes of Health, Grant Award Number DK 46971. As such, the United States Government may have certain rights to this invention.

FIELD OF THE INVENTION

The present invention provides compositions and methods for diagnosing Alzheimer's disease. In particular, the present invention provides modified beta-amyloid peptides, antibodies that specifically bind to the modified beta-amyloid peptides, and methods of use of these compositions in the diagnosis of Alzheimer's disease, as well as methods to monitor treatment and/or disease progression of Alzheimer's disease in patients. The present invention also provides compositions and methods useful in research involving amyloid precursor protein (APP) metabolism and Alzheimer's disease.

BACKGROUND OF THE INVENTION

Alzheimer's disease (AD) is the fourth most common cause of death in the United States, next to heart disease, cancer and stroke. It presently afflicts more than four million people, and this number is expected to double during the next forty years with the aging of the population. Alzheimer's disease is also the most common cause of chronic dementia, with approximately two million people in the United States suffering from dementia. At present, it is estimated that ten percent of the population older than 65 years of age have mild to severe dementia. This high prevalence, combined with the rate of growth of the elderly segment of the population, make dementia and particularly Alzheimer's disease, important current public health problems.

To date, Alzheimer's disease is the third most expensive disease in the United States, and costs approximately $100 billion each year. Costs associated with AD include direct medical costs such as nursing home care, direct nonmedical costs such as in-home day care, as well as indirect costs such as lost patient and care-giver productivity. Medical treatment may have economic benefits by slowing the rate of cognitive decline, delaying institutionalization, reducing care-giver hours, and improving quality of life.

Alzheimer's disease is a complex multi-genic neurodegenerative disorder characterized by progressive impairments in memory, behavior, language, and visuo-spatial skills, ending ultimately in death. Hallmark pathologies of Alzheimer's disease include granulovascular neuronal degeneration, extracellular neuritic plaques with β-amyloid deposits, intracellular neurofibrillary tangles and neurofibrillary degeneration, synaptic loss, and extensive neuronal cell death. It is now known that these histopathologic lesions of Alzheimer's disease correlate with the dementia observed in many elderly people.

Research on the causes of and treatments for Alzheimer's disease has led investigators down numerous avenues. Although many models have been proposed, no single model of AD satisfactorily accounts for all neuropathologic findings; nor do these models of AD satisfactorily account for the requirement of aging for disease onset. Cellular changes, leading to neuronal loss and the underlying etiology of the disease, remain unknown. Proposed causes include environmental factors (Perl, *Environmental Health Perspective* 63:149 [1985]), metal toxicity (Perl et al., *Science* 208:297 [1980]), defects in beta-amyloid protein metabolism (Shijo et al., *Science* 258:126 [1992]; and Kosik, *Science* 256:780 [1992]), and abnormal calcium homeostasis and/or calcium activated kinases (Mattson et al., *J. Neuroscience* 12:376 [1992]). The mechanisms of disease progression are equally unclear. Considerable human genetic evidence has implicated alterations in production or processing of the human amyloid precursor protein (APP) in the etiology of the disease. However, intensive research has proven that AD is a multifactorial disease with many different, perhaps overlapping, etiologies.

Early detection and identification of Alzheimer's disease facilitate prompt, appropriate treatment and care. However, there is currently no laboratory diagnostic test for Alzheimer's disease. Although studies have suggested that calcium imaging measurement in fibroblasts were of potential clinical use in diagnosing Alzheimer's disease (Peterson et al., *Neurobiology of Aging* 9:261 [1988]; and Peterson et al., *Proc. Natl. Acad. Sci. USA* 83:7999 [1986]), other studies using similar cell lines and techniques have shown no difference in calcium levels in Alzheimer's and normal control fibroblasts (Borden et al., *Neurobiology of Aging* 13:33 [1991]). Thus, there remains a need for diagnostic methods for Alzheimer's disease. In particular, reliable and cost-effective methods and compositions are needed to allow reliable diagnosis of Alzheimer's disease.

SUMMARY OF THE INVENTION

The present invention provides compositions and methods for diagnosing Alzheimer's disease. In particular, the present invention provides modified beta-amyloid peptides, antibodies that specifically bind to the modified beta-amyloid peptides, and methods of use of these compositions for the diagnosis of Alzheimer's disease. The present invention also provides compositions and methods useful in research involving amyloid precursor protein (APP) metabolism and Alzheimer's disease.

The present invention provides isolated and modified β-amyloid (βA) peptides comprising at least one malondialdehyde adduct. In one embodiment, the modified βA peptide comprises the amino acid sequence of SEQ ID NO:1. In another embodiment, the modified βA peptide comprises at least one malondialdehyde lysine adduct The present invention also provides purified antibodies directed against a modified β-amyloid peptide comprising at least one malondialdehyde adduct. In some embodiments, the antibody is a monoclonal antibody, while in other embodiments, the antibody is a polyclonal antibody. In other related embodiments, the invention provides compositions comprising the antibody directed against the modified βA -peptide comprising at least one malondialdehyde adduct.

The present invention further provides methods for detecting at least one modified β-amyloid peptide comprising at least one malondialdehyde adduct, comprising the steps of: providing a sample suspected of containing at least one modified β-amyloid peptide comprising at least one malondialdehyde adduct, and an antibody directed against at least on modified β-amyloid peptide comprising at least on malondialdehyde adduct; contacting the sample with the antibody under conditions such that the antibody specifically binds to the modified β-amyloid peptide comprising at least one malondialdehyde adduct, to form an antigen-antibody complex; and detecting the presence of the antigen-antibody complex. In some embodiments, the sample is selected from the group consisting of blood, plasma, serum, serous fluid, and cerebrospinal fluid. In some preferred embodiments, the sample is from a subject. In particularly preferred embodiments, the subject is a human. In further embodiments, the subject is selected from the group consisting of subjects displaying pathology resulting from Alzheimer's disease, subjects suspected of displaying pathology resulting from Alzheimer's disease, and subjects at risk of displaying pathology resulting from Alzheimer's disease. In some particularly preferred embodiments, the methods further comprise the step of diagnosing Alzheimer's disease. In additional particularly preferred embodiments, the Alzheimer's disease diagnosed using the methods of the present invention is selected from the group consisting of late onset Alzheimer's disease, early onset Alzheimer's disease, familial Alzheimer's disease and sporadic Alzheimer's disease. In some preferred embodiments, the methods further comprise the step of monitoring the efficacy of treatment of Alzheimer's disease.

In some preferred embodiments, the methods comprises an enzyme-linked immunosorbent assay. In particularly preferred embodiments, the enzyme-linked immunosorbent assay is selected from the group consisting of direct enzyme-linked immunosorbent assays, indirect enzyme-linked immunosorbent assays, direct sandwich enzyme-linked immunosorbent assays, indirect sandwich enzyme-linked immunosorbent assays, and competitive enzyme-linked immunosorbent assays. In alternative preferred embodiments, the antibody used in the methods of the present invention further comprises a conjugated enzyme, wherein the conjugated enzyme is selected from the group of enzymes consisting of horseradish peroxidases, alkaline phosphatases, ureases, glucoamylases, and β-galactosidases. In some particularly preferred embodiments, the enzyme-linked immunosorbent assay further comprises an alkaline phosphatase amplification system. In alternative preferred embodiments, the methods further comprise at least one capture antibody, while in still further embodiments, the methods further comprise at least one detection antibody wherein the detection antibody is directed against the antibody directed against the modified β-amyloid peptide comprising at least one malondialdehyde adduct. In still further embodiments, the detection antibody further comprises at least one conjugated enzyme selected from the group consisting of horseradish peroxidase, alkaline phosphatase, urease, glucoamylase and β-galactosidase. In still further preferred embodiments, the methods further comprise the step of quantitating the at least one modified β-amyloid peptide comprising at least one malondialdehyde adduct in the sample.

The present invention also provides kits for the detection of at least one modified β-amyloid peptide comprising at least one malondialdehyde adduct, comprising an immobilized support and at least one antibody directed against at least one modified modified β-amyloid peptide comprising at least one malondialdehyde adduct. In some preferred embodiments, the kit comprises an enzyme-linked immunosorbent assay kit. In still further embodiments, the kit further comprises components selected from the group consisting of needles, sample collection tubes, 96-well microtiter plates, instructions, at least one modified β-amyloid peptide comprising at least one malondialdehyde adduct, an antibody-enzyme conjugate directed against a modified β-amyloid peptide comprising at least one malondialdehyde adduct, at least one capture antibody, 96-well microtiter plates precoated with the at least one capture antibody, at least one coating buffer, at least one blocking buffer, distilled water, at least one enzyme-linked immunosorbent assay enzyme reaction substrate solution, and at least amplifier system. In some preferred embodiments, the amplifier system is an alkaline phosphatase enzyme-linked immunosorbent assay amplifier system.

The present invention also provides methods for detecting at least one antibody directed against a modified β-amyloid peptide comprising at least one malondialdehyde adduct, comprising: a) providing a sample suspected of containing at least one antibody directed against a modified β-amyloid peptide comprising at least one malondialdehyde adduct; at least one modified β-amyloid peptide having at least one malondiadehyde adduct, and a detection antibody; b) contacting the sample with the modified β-amyloid peptide, under conditions such that the antibody directed against a modified β-amyloid peptide comprising at least one malondialdehyde adduct specifically binds to the modified β-amyloid peptide to form an antigen-antibody complex; c) contacting the antigen-antibody complex with the detection antibody, under conditions such that the detection antibody specifically binds to the complex; and d) detecting the specific binding of the detection antibody to the antigen-antibody complex. In some preferred embodiments, the sample is selected from the group of samples consisting of blood, serous fluid, plasma, serum, cerebrospinal fluid, hybridoma conditioned culture medium, ascites fluid, and polyclonal antiserum. In some particularly preferred embodiments, the sample is from a subject, while in other preferred embodiments, the subject is human. In alternative preferred embodiments, the subject is selected from the group consisting of subjects displaying pathology resulting from Alzheimer's disease, subjects suspected of displaying pathology resulting from Alzheimer's disease, and subjects at risk of displaying pathology resulting from Alzheimer's disease. In still further preferred embodiments, the mehtods further comprise diagnosing Alzheimer's disease in the subject. In some preferred embodiments, the Alzheimer's disease is selected from the group consisting of late onset Alzheimer's disease, early onset Alzheimer's disease, familial Alzheimer's disease, and sporadic Alzheimer's disease. In preferred embodiments, the method comprises an enzyme-linked immunosorbent assay. In some preferred embodiments, the enzyme-linked immunosorbent assay is selected from the group consisting of direct enzyme-linked immunosorbent assays, indirect enzyme-linked immunosorbent assays, direct sandwich enzyme-linked immunosorbent assays, indirect sandwich enzyme-linked immunosorbent assays, and competitive enzyme-linked immunosorbent assays. In still further embodiments, the detection antibody further comprises a conjugated enzyme, wherein the conjugated enzyme is selected from the group of enzymes consisting of horseradish peroxidases, alkaline phosphatases, ureases, glucoamylases, and β-galactosidases. In additional embodiments, the enzyme-linked immunosorbent assay further comprises an alkaline phosphatase amplification system.

The present invention also provides kits for the detection of at least one antibody directed against at least one modified β-amyloid peptide comprising at least one malondialdehyde adduct, comprising an immobilized support, at least one purified and modified β-amyloid peptide comprising at least one malondialdehyde adduct, and at least one detection antibody. In some preferred embodiments, the kit is an enzyme-linked immunosorbent assay kit. In some preferred embodiments, the kit comprises components selected from the group consisting of needles, sample collection tubes, 96-well microtiter plates, instructions, at least one purified antibody directed against at least one β-amyloid peptide comprising at least one malondialdehyde adduct, at least one 96-well microtiter plate precoated with at least one β-amyloide peptide comprising at least one malondialdehyde adduct, at least one coating buffer, at least one blocking buffer, distilled water, at least one enzyme reaction substrate solution, and at least one amplifier system. In some particularly preferred embodiments, the amplifier system is an alkaline phosphatase enzyme-linked immunosorbent assay amplifier system.

DEFINITIONS

To facilitate an understanding of the present invention, a number of terms and phrases are defined below:

As used herein, the terms "peptide," "polypeptide" and "protein" all refer to a primary sequence of amino acids that are joined by covalent "peptide linkages." In general, a peptide consists of a few amino acids, typically from 2–50 amino acids, and is shorter than a protein. The term "polypeptide" encompasses peptides and proteins. In some embodiments, the peptide, polypeptide or protein is synthetic, while in other embodiments, the peptide, polypeptide or protein are recombinant or naturally occurring. A synthetic peptide is a peptide which is produced by artificial means in vitro (i.e., was not produced in vivo).

The terms "sample" and "specimen" are used in their broadest sense and encompass samples or specimens obtained from any source. As used herein, the term "sample" is used to refer to biological samples obtained from animals (including humans), and encompasses fluids, solids, tissues, and gases. In preferred embodiments of this invention, biological samples include cerebrospinal fluid (CSF), serous fluid, urine, saliva, blood, and blood products such as plasma, serum and the like. However, these examples are not to be construed as limiting the types of samples which find use with the present invention.

As used herein, the terms "beta-amyloid protein," "amyloid beta protein," "βA," "βA peptide" and "βA protein" all refer to a protein produced by neurons and glial cells in the brain. βA is found in the brain plaques of patients with Alzheimer's disease, head trauma and Down's syndrome, and is also found normally in the spinal fluid and blood (See e.g., Haass and Selkoe, Cell 75:1039 [1993]; Teller et al, Nature Med., 2:93 [1996]).

As used herein, the term "modified βA peptide" refers to a beta-amyloid peptide. In preferred embodiments, the modified βA peptide has been oxidatively modified. In a particularly preferred embodiment, the modified βA peptide is oxidatively modified by oxidative stress.

As used herein, the terms "modified β-amyloid peptide comprising at least one malondialdehyde adduct" or "βA-MDA" refer to a βA peptide that has been modified by the covalent addition of at least one malondialdehyde group. In some embodiments, the MDA group is added using an oxidative stress-induced modification reaction (i.e., an oxidation reaction). In one preferred embodiment, the modified β-amyloid peptide comprising at least one malondialdehyde adduct comprises a malondialdehyde-lysine adduct.

As used herein, the term "oxidative stress" refers to the cytotoxic effects of oxygen radicals (i.e., superoxide anion $[.O_2.^-]$, hydroxy radical $[.OH]$, and hydrogen peroxide $[H_2O_2]$), generated as byproducts of metabolic processes that utilize molecular oxygen (See e.g., Coyle et al., Science 262:689–695 [1993]).

As used herein, the terms "host," "subject" and "patient" refer to any animal, including but not limited to, human and non-human animals (e.g., rodents, arthropods, insects [e.g., Diptera], fish [e.g., zebrafish], non-human primates, ovines, bovines, ruminants, lagomorphs, porcines, caprines, equines, canines, felines, aves, etc.), which is studied, analyzed, tested, diagnosed or treated. As used herein, the terms "host," "subject" and "patient" are used interchangeably.

As used herein, the terms "Alzheimer's disease" and "AD" refer to a neurodegenerative disorder and encompasses familial Alzheimer's disease and sporadic Alzheimer's disease. The term "familial Alzheimer's disease" refers to Alzheimer's disease associated with genetic factors (i.e., demonstrates inheritance) while "sporadic Alzheimer's disease" refers to Alzheimer's disease that is not associated with prior family history of the disease. Symptoms indicative of Alzheimer's disease in human subjects typically include, but are not limited to, mild to severe dementia, progressive impairment of memory (ranging from mild forgetfulness to disorientation and severe memory loss), poor visuo-spatial skills, personality changes, poor impulse control, poor judgement, distrust of others, increased stubbornness, restlessness, poor planning ability, poor decision making, and social withdrawal. In severe cases, patients lose the ability to use language and communicate, and require assistance in personal hygiene, eating and dressing, and are eventually bedridden. Hallmark pathologies within brain tissue include extracellular neuritic β-amyloid plaques, neurofibrillary tangles, neurofibrillary degeneration, granulovascular neuronal degeneration, synaptic loss, and extensive neuronal cell death.

As used herein, the term "early-onset Alzheimer's disease" refers to the classification used in Alzheimer's disease cases diagnosed as occurring before the age of 65. As used herein, the term "late-onset Alzheimer's disease" refers to the classification used in Alzheimer's disease cases diagnosed as occurring after the age of 65.

As used herein, the terms "subject having Alzheimer's disease" or "subject displaying symptoms or pathology indicative of Alzheimer's disease" "subjects suspected of displaying symptoms or pathology indicative of Alzheimer's disease" refer to a subject that is identified as having or likely to have Alzheimer's disease based on known Alzheimer's symptoms and pathology.

As used herein, the term "subject at risk of displaying pathology indicative of Alzheimer's disease" refers to a subject identified as being at risk for developing Alzheimer's disease (e.g., because of a familial inheritance pattern of Alzheimer's disease in the subject's family).

As used herein, the term "lesion" refers to a wound or injury, or to a pathologic change in a tissue. For example, the amyloid plaque lesions observed in the brains of patients having Alzheimer's disease are considered the hallmark pathology characteristic of the disease.

As used herein, the term "antibody" (or "antibodies") refers to any immunoglobulin that binds specifically to an antigenic determinant, and specifically, binds to proteins identical or structurally related to the antigenic determinant which stimulated their production. Thus, antibodies are useful in assays to detect the antigen which stimulated their production. Monoclonal antibodies are derived from a single clone of B lymphocytes (i.e., B cells), and are generally homogeneous in structure and antigen specificity. Polyclonal antibodies originate from many different clones of antibody-producing cells, and thus are heterogenous in their structure and epitope specificity, but all recognize the same antigen. In some embodiments, monoclonal and polyclonal antibodies are used as crude preparations, while in preferred embodiments, these antibodies are purified. For example, in some embodiments, polyclonal antibodies contained in crude antiserum are used. Also, it is intended that the term "antibody" encompass any immunoglobulin (e.g., IgG, IgM, IgA, IgE, IgD, etc.) obtained from any source (e.g., humans, rodents, non-human primates, lagomorphs, caprines, bovines, equines, ovines, etc.).

As used herein, the terms "auto-antibody" or "auto-antibodies" refer to any immunoglobulin that binds specifically to an antigen that is native to the host organism that produced the antibody (i.e., the antigen is directed against "self" antigens). The presence of auto-antibodies is referred to herein as "autoimmunity."

As used herein, the term "antigen" is used in reference to any substance that is capable of being recognized by an antibody. It is intended that this term encompass any antigen and "immunogen" (i.e., a substance which induces the formation of antibodies). Thus, in an immunogenic reaction, antibodies are produced in response to the presence of an antigen or portion of an antigen. The terms "antigen" and "immunogen" are used to refer to an individual macromolecule or to a homogeneous or heterogeneous population of antigenic macromolecules. It is intended that the terms antigen and immunogen encompass protein molecules or portions of protein molecules, which contains one or more epitopes. In many cases, antigens are also immunogens, thus the term "antigen" is often used interchangeably with the term "immunogen." In some preferred embodiments, immunogenic substances are used as antigens in assays to detect the presence of appropriate antibodies in the serum of an immunized animal.

As used herein, the terms "antigen fragment" and "portion of an antigen" and the like are used in reference to a portion of an antigen. Antigen fragments or portions typcially range in size, from a small percentage of the entire antigen to a large percentage, but not 100%, of the antigen. However, in situations where "at least a portion" of an antigen is specified, it is contemplated that the entire antigen is also present (i.e., it is not intended that the sample tested contain only a portion of an antigen). In some embodiments, antigen fragments and/or portions therof, comprise an "epitope" recognized by an antibody, while in other embodiments these fragments and/or portions do not comprise an epitope recognized by an antibody. In addition, in some embodiments, antigen fragments and/or portions are not immunogenic, while in preferred embodiments, the antigen fragments and/or portions are immunogenic.

The terms "antigenic determinant" and "epitope" as used herein refer to that portion of an antigen that makes contact with a particular antibody variable region. When a protein or fragment (or portion) of a protein is used to immunize a host animal, numerous regions of the protein are likely to induce the production of antibodies which bind specifically to a given region or three-dimensional structure on the protein (these regions and/or structures are referred to as "antigenic determinants"). In some settings, antigenic determinants compete with the intact antigen (i.e., the "immunogen" used to elicit the immune response) for binding to an antibody.

The terms "specific binding" and "specifically binding" when used in reference to the interaction between an antibody and an antigen describe an interaction that is dependent upon the presence of a particular structure (i.e., the antigenic determinant or epitope) on the antigen. In other words, the antibody recognizes and binds to a protein structure unique to the antigen, rather than binding to all proteins in general (i.e., non-specific binding).

As used herein the term "immunogenically-effective amount" refers to that amount of an immunogen required to invoke the production of protective levels of antibodies in a host upon vaccination.

As used herein, the term "adjuvant" is defined as a substance which enhances the immunogenicity of a coadministered antigen. If adjuvant is used, it is not intended that the present invention be limited to any particular type of adjuvant—or that the same adjuvant, once used, be used for all subsequent immunizations. The present invention contemplates many adjuvants, including but not limited to, keyhole limpet hemocyanin (KLH), agar beads, aluminum hydroxide or phosphate (alum), Freund's adjuvant (incomplete or complete), Quil A adjuvant and Gerbu adjuvant (Accurate Chemical and Scientific Corporation), and bacterins (i.e., killed preparations of bacterial cells, especially mycoplasma).

As used herein, the terms "purified" and "to purify" and "purification" refers to the removal or reduction of at least one contaminant from a sample. For example, antibodies are purified by removal of contaminating non-immunoglobulin proteins. Antibodies are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample (i.e., "enrichment" of an antibody).

As used herein, the term "immunoassay" refers to any assay that uses at least one specific antibody for the detection or quantitation of an antigen. Immunoassays include, but are not limited to, Western blots, ELISAs, radio-immunoassays, and immunofluorescence assays. Furthermore, many different ELISA formats are known to those in the art, any of which will find use in the present invention. However, it is not intended that the present invention be limited to these assays. In additional embodiments, other antigen-antibody reactions are used in the present invention, including but not limited to "flocculation" (i.e., a colloidal suspension produced upon the formation of antigen-antibody complexes), "agglutination" (i.e., clumping of cells or other substances upon exposure to antibody), "particle agglutination" (i.e., clumping of particles coated with antigen in the presence of antibody or the clumping of particles coated with antibody in the presence of antigen), "complement fixation" (i.e., the use of complement in an antibody-antigen reaction method), and other methods commonly used in serology, immunology, immunocytochemistry, immunohistochemistry, and related fields.

The terms "Western blot," "Western immunoblot" "immunoblot" and "Western" refer to the immunological analysis of protein(s), polypeptides or peptides that have been immobilized onto a membrane support. The proteins are first resolved by polyacrylamide gel electrophoresis (i.e., SDS-PAGE) to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody which specifically binds the primary antibody. The secondary antibody is typically conjugated to an enzyme which permits visualization of the antigen-antibody complex by the production of a colored reaction product or catalyzes a luminescent enzymatic reaction (e.g., the ECL reagent, Amersham).

As used herein, the term "ELISA" refers to enzyme-linked immunosorbent assay (or EIA). Numerous ELISA methods and applications are known in the art, and are described in many references (See, e.g., Crowther, "Enzyme-Linked Immunosorbent Assay (ELISA)," in *Molecular Biomethods Handbook*, Rapley et al. [eds.], pp. 595–617, Humana Press, Inc., Totowa, N.J. [1998]; Harlow and Lane (eds.), *Antibodies: A Laboratory Manual*, Cold Spring Harbor Laboratory Press [1988]; Ausubel et al. (eds.), *Current Protocols in Molecular Biology*, Ch. 11, John Wiley & Sons, Inc., New York [1994]). In addition, there are numerous commercially available ELISA test systems.

One of the ELISA methods used in the present invention is a "direct ELISA," where an antigen (e.g., βA-MDA peptide) in a sample is detected. In one embodiment of the direct ELISA, a sample containing antigen is exposed to a solid (i.e., stationary or immobilized) support (e.g., a microtiter plate well). The antigen within the sample becomes immobilized to the stationary phase, and is detected directly using an enzyme-conjugated antibody specific for the antigen.

In an alternative embodiment, an antibody specific for an antigen is detected in a sample. In this embodiment, a sample containing an antibody (e.g., an anti-βA-MDA antibody) is immobilized to a solid support (e.g., a microtiter plate well). The antigen-specific antibody is subsequently detected using purified antigen and an enzyme-conjugated antibody specific for the antigen.

In an alternative embodiment, an "indirect ELISA" is used. In one embodiment, an antigen (or antibody) is immobilized to a solid support (e.g., a microtiter plate well) as in the direct ELISA, but is detected indirectly by first adding an antigen-specific antibody (or antigen), then followed by the addition of a detection antibody specific for the antibody that specifically binds the antigen, also known as "species-specific" antibodies (e.g., a goat anti-rabbit antibody), which are available from various manufacturers known to those in the art (e.g., Santa Cruz Biotechnology; Zymed; and Pharmingen/Transduction Laboratories).

In other embodiments, a "sandwich ELISA" is used, where the antigen is immobilized on a solid support (e.g., a microtiter plate) via an antibody (i.e., a capture antibody) that is immobilized on the solid support and is able to bind the antigen of interest. Following the affixing of a suitable capture antibody to the immobilized phase, a sample is then added to the microtiter plate well, followed by washing. If the antigen of interest is present in the sample, it is bound to the capture antibody present on the support. In some embodiments, a sandwich ELISA is a "direct sandwich" ELISA, where the captured antigen is detected directly by using an enzyme-conjugated antibody directed against the antigen. Alternatively, in other embodiments, a sandwich ELISA is an "indirect sandwich" ELISA, where the captured antigen is detected indirectly by using an antibody directed against the antigen, which is then detected by another enzyme-conjugated antibody which binds the antigen-specific antibody, thus forming an antibody-antigen-antibody-antibody complex. Suitable reporter reagents are then added to detect the third antibody. Alternatively, in some embodiments, any number of additional antibodies are added as necessary, in order to detect the antigen-antibody complex. In some preferred embodiments, these additional antibodies are labelled or tagged, so as to permit their visualization and/or quantitation.

As used herein, the term "capture antibody" refers to an antibody that is used in a sandwich ELISA to bind (i.e., capture) an antigen in a sample prior to detection of the antigen. For example, in some embodiments, the polyclonal anti-βA-MDA antibody of the present invention serves as a capture antibody when immobilized in a microtiter plate well. This capture antibody binds βA-MDA antigen present in a sample added to the well. In one embodiment of the present invention, biotinylated capture antibodies are used in the present invention in conjunction with avidin-coated solid support. Another antibody (i.e., the detection antibody) is then used to bind and detect the antigen-antibody complex, in effect forming a "sandwich" comprised of antibody-antigen-antibody (i.e., a sandwich ELISA).

As used herein, a "detection antibody" is an antibody which carries a means for visualization or quantitation, which is typically a conjugated enzyme moiety that typically yields a colored or fluorescent reaction product following the addition of a suitable substrate. Conjugated enzymes commonly used with detection antibodies in the ELISA include horseradish peroxidase, urease, alkaline phosphatase, glucoamylase and β-galactosidase. In some embodiments, the detection antibody is directed against the antigen of interest, while in other embodiments, the detection antibody is not directed against the antigen of interest. In some embodiments, the detection antibody is an anti-species antibody. Alternatively, the detection antibody is prepared with a label such as biotin, a fluorescent marker, or a radioisotope, and is detected and/or quantitated using this label.

As used herein, the terms "reporter reagent," "reporter molecule," "detection substrate" and "detection reagent" are used in reference to reagents which permit the detection and/or quantitation of an antibody bound to an antigen. For example, in some embodiments, the reporter reagent is a colorimetric substrate for an enzyme that has been conjugated to an antibody. Addition of a suitable substrate to the antibody-enzyme conjugate results in the production of a colorimetric or fluorimetric signal (e.g., following the binding of the conjugated antibody to the antigen of interest). Other reporter reagents include, but are not limited to, radioactive compounds. This definition also encompasses the use of biotin and avidin-based compounds (e.g., including but not limited to neutravidin and streptavidin) as part of the detection system.

As used herein, the term "signal" is used generally in reference to any detectable process that indicates that a reaction has occurred, for example, binding of antibody to antigen. It is contemplated that signals in the form of radioactivity, fluorimetric or colorimetric products/reagents will all find use with the present invention. In various embodiments of the present invention, the signal is assessed qualitatively, while in alternative embodiments, the signal is assessed quantitatively.

As used herein, the term "amplifier" is used in reference to a system which enhances the signal in a detection method, such as an ELISA (e.g., an alkaline phosphatase amplifier system used in an ELISA).

As used herein, the term "solid support" is used in reference to any solid or stationary material to which reagents such as antibodies, antigens, and other test components are attached. For example, in the ELISA method, the wells of microtiter plates provide solid supports. Other examples of solid supports include microscope slides, coverslips, beads, particles, cell culture flasks, as well as many other suitable items.

As used herein, the term "kit" is used in reference to a combination of reagents and other materials which facilitate sample analysis. In some embodiments, the immunoassay kit of the present invention includes a suitable capture antibody, reporter antibody, antigen, detection reagents and amplifier system. Furthermore, in other embodiments, the kit includes, but is not limited to, components such as apparatus for sample collection, sample tubes, holders, trays, racks, dishes, plates, instructions to the kit user, solutions or other chemical reagents, and samples to be used for standardization, normalization, and/or control samples.

As used herein, the term "in vitro" refers to an artificial environment and to processes or reactions that occur within an artificial environment. In vitro environments consist of, but are not limited to, controlled laboratory conditions. The term "in vivo" refers to the natural environment (e.g., an animal or a cell) and to processes or reactions that occur within that natural environment.

DESCRIPTION OF THE INVENTION

The present invention provides compositions and methods for diagnosing Alzheimer's disease. In particular, the present invention provides methods for diagnosing Alzheimer's disease using antibodies that specifically bind to modified beta amyloid peptides indicative of Alzheimer's disease.

Deposition of cerebral amyloid is a primary neuropathologic marker of Alzheimer's disease (AD). This amyloid is composed of a 40–42 amino acid peptide known as the beta amyloid peptide (βA) (Glenner et al., *Biochem. Biophys. Res. Commun.*, 120:885–890 [1984]). Amyloid deposits in AD are found mainly as components of senile plaques, and in the walls of cerebral and meningeal blood vessels (Robakis et al., *Neurobiol. Aging* 15:S127–129 [1994]). βA is also produced during normal cellular metabolism (Haass et al., *Nature* 359:322–324 [1992]; Shoji et al., *Science* 258:126–129 [1992]).

Molecular cloning showed that βA comprises a small region of a larger amyloid precursor protein (i.e., "APP") (Robakis et al., *Proc. Natl. Acad. Sci. USA* 84:4190–4194 [1987]; and Weidemann et al., *Cell* 57:115–126 [1989]). The APP protein is a type I integral membrane glycoprotein having a large extracytoplasmic portion, a smaller intracytoplasmic region, and a single transmembrane domain. APP undergoes extensive post-translational modifications prior to the secretion of its N-terminal portion (See e.g., Pappolla et al., in "Perspectives in behavioral medicine, Alzheimer's disease and AIDS," Stein et al. [eds.], Academic Press, San Diego, Calif., pp. 3–20 [1995]; and Robakis et al., *Neurobiol. Aging* 15:S127–129 [1994]). Physiologic processing of APP involves cleavage within the βA sequence by an uncloned enzymatic activity, termed alpha-secretase (Anderson et al., *Neurosci. Lett.*, 128:126–129 [1991]). Smaller quantities of APP molecules are cleaved at two other sites that potentially produce amyloidogenic secreted or membrane bound APP (Robakis et al., 1994, supra).

Although it is not clear whether beta-amyloid accumulation causes Alzheimer's disease or is an effect of Alzheimer's disease, considerable evidence has strengthened the view that amyloid accumulation is the causative agent of Alzheimer's disease. However, it is not necessary to understand the cause or effect of beta-amyloid accumulation in Alzheimer's disease in order to practice the present invention, nor is it intended that the present invention be limited to any particular mechanism or mechanisms of disease genesis or toxicity. Indeed, an understanding of any of the mechanisms of pathogenesis are not necessary in order to use the present invention.

First, several point mutations within the APP gene which segregate within a subgroup of patients afflicted with a familial form of the disorder have been identified, thereby suggesting a pathogenetic relationship between the APP gene and AD (Chartier-Harlin et al., *Nature* 353:844–846 [1991]; and Kennedy et al, *Brain* 116:3009–324 [1993]). Second, amyloid deposition temporally precedes the development of neurofibrillary changes (Pappolla et al., *Mol. Chem. Neuropathol.*, 28:21–34 [1996]). This observation is also consistent with a link between amyloid and neuronal degeneration. Finally, it has been shown that βA has neurotoxic properties (Yankner et *al., Science* 250:279–282 [1990]; and Behl et al., *Biochem. Biophys. Res. Commun.*, 186:944–950 [1992]). Although the mechanism of toxicity is not totally understood, βA neurotoxicity provides a possible connection between amyloid accumulation and neurodegeneration. In addition to free-radicals, increased sensitivity to excitotoxicity and/or disruption of $Ca^{2+}$, homeostasis seems to be involved (See e.g., Copani et al., *Molecular Pharmacology* 47:890–897 [1995]; Mattson et al., *Trends Neurosci.*, 16:409–414 [1993]; Le et al., *Brain Res.*, 686:49–60 [1995]; and Mark et al., *J. Neurosci.*, 15:6239–6249 [1995]). The magnitude of the damage contributed by each of these factors and the extent of their interaction are not clear (Copani et al., 1995, supra). However, it is not necessary to understand the cause or effect of beta-amyloid accumulation in Alzheimer's disease in order to practice the present invention, nor is it intended that the present invention be limited to any particular mechanism or mechanisms of disease genesis or toxicity. Indeed, an understanding of any of the mechanisms of pathogenesis are not necessary in order to use the present invention.

Because of the close association between aging and AD and the similarities in the neuropathology observed in both conditions, oxidative stress has been proposed to play a role in the pathogenesis of Alzheimer's disease. It is believed that oxidative stress introduces oxidative modifications in βA before and/or after its secretion into the extracellular matrix. Furthermore, it is contemplated that circulating βA in individuals having Alzheimer's disease, brain trauma or Down's syndrome, but not in individuals without neurological injury, have specific post-translational chemical modifications. However, an understanding of the mechanism(s) involved in Alzheimer's disease pathogenesis is not necessary in order to practice the present invention, nor is it intended that the present invention be limited to any particular mechanism(s) of disease pathogenesis.

In one embodiment, the present invention provides modified βA synthetic peptides. A commercially available βA synthetic polypeptide 1–42 (SEQ ID NO: 1, Sigma, Catalog No. A9810) was chemically modified in vitro to produce a βA peptide containing malondialdehyde adduct(s) (See, Example 1). The unmodified peptide has the sequence:

Asp-Ala-Glu-Phe-Arg-His-Asp-Ser-Gly-    (SEQ ID NO:1)

Tyr-Glu-Val-His-His-Gln-Lys-Leu-Val-

Phe-Phe-Ala-Glu-Asp-Val-Gly-Ser-Asn-

Lys-Gly-Ala-Ile-Ile-Gly-Leu-Met-Val-

Gly-Gly-Val-Val-Ile-Ala

This βA peptide with a malondialdehyde adduct modification is referred to herein as "βA-MDA." It has been shown previously that protein-MDA adducts are formed by the modification of lysine residues. However, it is not intended that the present invention be limited to malondialdehyde adducts formed on lysine residues of the βA peptide. As oxidative stress is implicated in the aging process, it is contemplated that oxidative stress modifications (e.g., the presence of malondialdehyde adduct[s]) are associated with βA peptides in patients having Alzheimer's disease.

However, an understanding of the mechanism of oxidative stress modifications or modified βA-peptides is not necessary to make or use the present invention. Also it is not intended that the present invention be limited to this one type of modification.

In another embodiment (e.g., as described in Example 2), synthetic βA-MDA peptide (e.g., produced as described in Example 1) was used to raise anti-βA-MDA polyclonal antiserum in rabbits. Briefly, the βA-MDA peptide was conjugated to keyhole limpet hemocyanin (KLH), mixed with Freund's incomplete adjuvant, and used to immunize New Zealand white rabbits at 8–10 subcutaneous dorsal sites using standard methods. The animals received boosts at 4, 6 and 8 weeks after the initial immunization. Bleeds were obtained at weeks 8, 12 and 16 following the initial immunization. The presence of anti-βA-MDA antibody in the rabbits' sera was tested using a Western immunoblot technique (e.g., as described in Example 4). The polyclonal antibody was purified using a combination of ammonium sulfate precipitation and immunoaffinity purification, as known in the art.

It is not intended that the production of antibody of the present invention be limited to any particular method. Indeed, it is contemplated that the antibody be prepared by any suitable method. In addition, polyclonal as well as monoclonal antibodies find use in the present invention. Indeed, the present invention also provides methods for the production of monoclonal antibody directed against βA-MDA peptide (e.g., as described in Example 3). Numerous methods for the production and purification of monoclonal and polyclonal antibodies are well known in the art (See e.g., Sambrook et al. (eds.), Molecular Cloning, Cold Spring Harbor Laboratory Press [1989]; Harlow and Lane (eds.), *Antibodies: A Laboratory Manual*, Cold Spring Harbor Laboratory Press [1988]; Ausubel et al. (eds.), *Current Protocols in Molecular Biology*, p. 11.4.2–11.15.4, John Wiley & Sons, Inc., New York [1994]; Köhler and Milstein, Nature 256:495–497 [1975]; Kozbor et al., *Immunol. Today* 4:72 [1983]; and Cole et al., in *Monoclonal Antibodies and Cancer Therapy*, Alan R. Liss, Inc., pp. 77–96 [1985]).

In addition, in other embodiments, any suitable modified βA peptide or fragment thereof, is used as an immunogen. In some embodiments, the immunogen is native, while in other embodiments, the immunogen is synthetic (i.e., recombinant or produced by in vitro chemical synthesis). Similarly, it is not intended that the present invention be limited to any particular βA-derived immunogen, immunization method, immunization schedule, animal species, test protocol for determining antibody production or antibody purification method.

In some embodiments, the antibody preparation of the present invention is purified from crude antiserum, hybridoma or cell culture supernatant, ascites fluid, or other starting material using any conventional method. Such purification methods include, but are not limited to, protein A affinity, protein G affinity, ammonium sulfate precipitation, ion exchange chromatography, gel filtration, and immunoaffinity chromatography (See, e.g., Harlow and Lane (eds.), *Antibodies: A Laboratory Manual*, Cold Spring Harbor Laboratory Press [1988]; and Ausubel et al. (eds.), *Current Protocols in Molecular Biology*, Ch. 11, John Wiley & Sons, Inc., New York [1994]).

The antibodies of the present invention find numerous uses, including Western blotting, enzyme-linked immunosorbent assays (ELISAs), radioimmunoassays (RIAs), immunofluorescence assays (IFAs), immunoprecipitation, immunohistochemistry and clinical diagnostic applications using methods known in the art (See e.g., Harlow and Lane (eds.), *Antibodies: A Laboratory Manual*, Cold Spring Harbor Laboratory Press [1988]; Ausubel et al. (eds.), *Current Protocols in Molecular Biology*, Vol. 1–4, John Wiley & Sons, Inc., New York [1994]; and Laurino et al., *Ann. Clin. Lab Sci.*, 29(3):158–166 [1999]).

The specificity of a polyclonal antibody produced during the development of the present invention was tested in a Western immunoblot (e.g., as described in Example 4, below). In this protocol, purified polyclonal anti-βA-MDA antibody (e.g., produced as described in Example 2) was used as the primary antibody, and a goat-anti-rabbit IgG-horse radish peroxidase (HRPO) conjugated antibody (Santa Cruz) was used as the secondary antibody. Briefly, βA-MDA and unmodified βA synthetic peptide samples were prepared for analysis in Laemmli buffer. Peptide samples were resolved using denaturing polyacrylamide gel electrophoresis (i.e., SDS-PAGE) and electroblotted onto nitrocellulose. Blots were incubated overnight in blocking buffer with anti-βA-MDA antibody at a 1:1,000 dilution. Membranes were washed, then incubated with HRPO-conjugated goat anti-rabbit IgG (Santa Cruz) diluted to 1:5,000 in blocking buffer. Following this incubation, blots were washed 3 times, then incubated in chemiluminescent detection substrate and the signal detected on X-ray film. This experiment demonstrated that the anti-βA-MDA antibody detected βA-MDA synthetic peptide, but not unmodified peptide. The preimmune serum showed no reactivity towards the same samples.

Following the establishment of the specificity of the anti-βA-MDA antibody of the present invention, the antibody was used to detect endogenous βA-MDA forms in human brain cortex tissue from an Alzheimer's patient and a matched control individual without Alzheimer's disease (as described in Examples 5 and 6, below).

Briefly, lysates were produced from these two brain tissues. These brain cortex tissue lysates were then subjected to immunoprecipitation, using 2 μg of an anti-βA antibody (Transduction Laboratories, Affinity Research Products Catalog No. AK6905) and Protein-A-agarose beads. The resulting immunoprecipitates were fractionated using SDS-PAGE and analyzed in a Western immunoblot (e.g., as described in Example 4), where the anti-βA-MDA antibody of the present invention was used as the primary antibody, and an HRPO-conjugated goat-anti-rabbit antibody was the secondary antibody.

Figure 1:
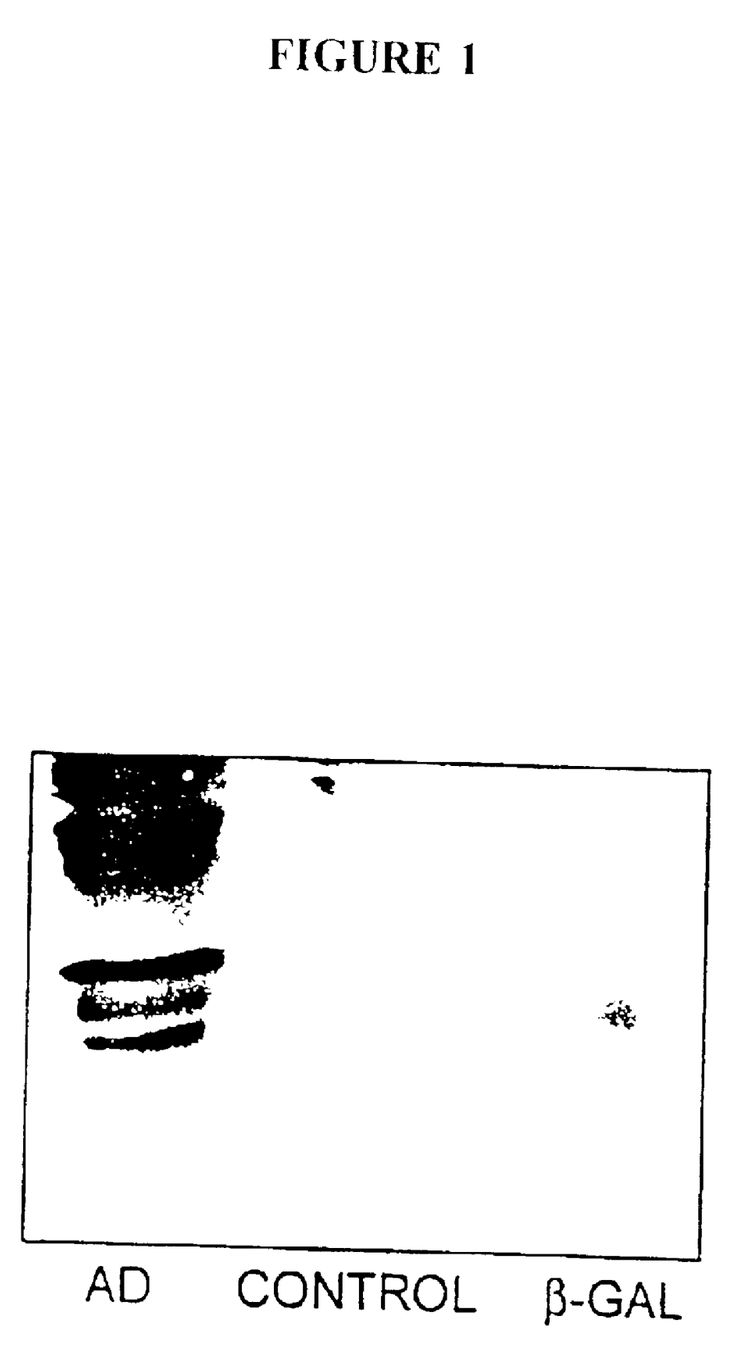
FIG. 1 provides the results of a Western immunoblot assay using a primary antibody having binding specificity for a modified β-amyloid peptide comprising at least one malondialdehyde adduct and brain tissue lysate samples.

As shown in FIG. 1, this experiment demonstrates that at least one protein present in the brain tissue βA-immunoprecipitate of an Alzheimer's disease patient (lane indicated as "AD") was recognized by the anti-βA-MDA antibody. However, no such bands were detected in the lane containing immunoprecipitate from the control (i.e., disease-free individual; lane indicated as "CONTROL"). A single, predominant reacting protein band was also observed when using crude brain tissue lysates that had not been immunoprecipitated using the anti-βA antibody.

The specificity of the primary and secondary antibodies were further confirmed by immunoprecipitation and Western blot analysis using an anti-β-galactosidase antibody and brain tissue from an Alzheimer's disease patient. This immunoprecipitate was blotted and probed in parallel with the AD and CONTROL samples used in the blot shown in FIG. 1 using the same anti-βA-MDA primary antibody and the HRPO-conjugated secondary antibody (lane indicated as "β-GAL"). As shown in FIG. 1, the anti-βA-MDA primary antibody showed no reactivity towards the anti-β-galactosidase immunoprecipitate from the brain tissue of the Alzheimer's patient. Furthermore, in a separate experiment, it was found that the antibody that detects unmodified βA polypeptide when used as the primary antibody, detected identical bands in the immunoprecipitated brain tissues from an Alzheimer's disease patient and a disease-free control individual.

Thus, polyclonal anti-βA-MDA antibody (e.g., produced as described in Example 2), recognizes a modified endogenous βA-MDA peptide that is found only in the brain of an individual having Alzheimer's disease, but not in the brain of an unaffected individual. Thus, the present invention provides compositions and methods for post-mortem diagnosis of Alzheimer's disease.

It is known that βA is present in human blood and cerebrospinal fluid (CSF) of living subjects. It is contemplated that βA-MDA is also present in the blood, serous fluid and/or CSF of living subjects. It is contemplated that the presence of βA-MDA, or its presence above a threshold level, in these fluids is diagnostic of Alzheimer's disease. Thus, the present invention provides methods and compositions for the diagnosis and prognosis of Alzheimer's disease. Indeed, the present invention provides compositions and methods to analyze disease severity, and the efficacy of Alzheimer's disease therapies. It is contemplated that subjects identified as having higher levels of βA-MDA (e.g., in blood, serous fluid or CSF) have more advanced Alzheimer's disease than subjects showing lower levels of βA-MDA. It is contemplated that by monitoring the levels of βA-MDA in blood, serous fluid and/or CSF of patients undergoing treatment for Alzheimer's disease, determinations regarding the effectiveness of treatment regimes are possible. For example, reduced levels of βA-MDA over time indicate that the treatment used to treat a subject with Alzheimer's disease is effective.

It is contemplated that the present invention will find use in testing subjects such as those who have been previously diagnosed with Alzheimer's disease, those who are suspected of having Alzheimer's disease, and those at risk of developing Alzheimer's disease. For example, patients diagnosed with dementia, in particular, those patients who were previously clinically normal, are suitable subjects. However, it is not intended that the present invention be limited to use with any particular subject or patient types. The methods of the present invention are also useful for detecting early onset Alzheimer's disease and late onset Alzheimer's disease, as well as for detecting sporadic Alzheimer's disease and familial Alzheimer's disease.

The present invention also provides compositions and methods for the detection and quantitation (i.e., measurement) of βA-MDA peptide in the blood, serous fluid and CSF. Standard techniques known in the art are easily adapted to quantitate the levels of circulating βA-MDA peptide in blood, serous fluid and/or CSF samples, including but not limited to, ELISA.

Factors contributing to the success of the ELISA methods of the present invention include their sensitivity, versatility, long reagent shelf-life, ease of preparation of reagents, non-radioactive reagents, and assay speed. Furthermore, in some embodiments, the assay is quantitative. In addition, reagents and equipment designed specifically for use in ELISA protocols are readily available from numerous manufacturers, including Pierce Chemical Company, Bio-Rad, Dynatech Industries, GibcoBRL/Life Technologies, Fisher Scientific, and Promega.

Many ELISA applications and formats have been described. Various sources provide discussion of ELISA chemistry, applications, and detailed protocols (See e.g., Crowther, "Enzyme-Linked Immunosorbent Assay (ELISA)," in *Molecular Biomethods Handbook*, Rapley et al. [eds.], pp. 595–617, Humana Press, Inc., Totowa, N.J. [1998]; Harlow and Lane (eds.), *Antibodies. A Laboratory Manual*, Cold Spring Harbor Laboratory Press [1988]; Ausubel et al. (eds.), *Current Protocols in Molecular Biology*, Ch. 11, John Wiley & Sons, Inc., New York [1994]; and Laurino et al., *Ann. Clin. Lab Sci.*, 29(3):158–166 [1999]).

In preferred embodiments of the present invention, ELISA methods for quantitation of antigen are provided. In some of these methods, the antigen (e.g., the βA-MDA peptide) is first immobilized on a solid support (e.g. in a microtiter plate well). Detection and quantitation of the immobilized antigen is accomplished by use of an antibody-enzyme conjugate capable of binding to the immobilized antigen and producing a quantifiable signal. In some embodiments, the amount of antigen present is directly proportional to the amount of enzyme reaction product produced after the addition of an appropriate enzyme substrate.

As indicated previously, enzymes commonly used in ELISAs include horseradish peroxidase (HRPO), urease, alkaline phosphatase, glucoamylase and β-galactosidase. Protocols for the preparation of suitable antibody-enzyme conjugates are well known in the art. The present invention provides methods for the preparation of an antibody-enzyme (i.e., HRPO enzyme) conjugate that specifically recognizes the antigen of interest (i.e., βA-MDA peptide) for use in immunoassay (e.g., ELISA) methods for detection of Alzheimer's disease. It is not intended that the present invention be limited to the antibody-enzyme conjugation method provided herein, as those of skill in the art will recognize other methods for antibody-enzyme conjugation that find use with the present invention.

Conjugation of enzymes to antibodies involves the formation of a stable, covalent linkage between an enzyme (e.g., HRPO or alkaline phosphatase) and the antibody (e.g., the polyclonal anti-βA-MDA antibody), where neither the antigen-binding site of the antibody nor the active site of the enzyme is functionally altered.

The conjugation of antibody and HRPO is dependent on the generation of aldehyde groups by periodate oxidation of the carbohydrate moieties on HRPO (Nakane and Kawaoi, *J. Histochem. Cytochem.*, 22:1084–1091 [1988]). Combination of these active aldehydes with amino groups on the antibody forms Schiff bases that, upon reduction by sodium borohydride, become stable.

Protocols to make antibody-enzyme conjugates using urease or alkaline phosphatase enzymes are also known in the art (Healey et al., *Clin. Chim. Acta* 134:51–58 [1983]; Voller et al., *Bull. W.H.O.*, 53:55–65 [1976]; and Jeanson et al., *J. Immunol. Methods* 111:261–270 [1988]). For urease conjugation, cross-linking of the urease enzyme (e.g., Urease Type VII, Sigma No. U0376) and antibody using m-maleimidobenzoyl N-hydroxysuccinimide ester (MBS) is achieved through benzoylation of free amino groups on the antibody. This is followed by thiolation of the maleimide moiety of MBS by the cysteine sulfhydryl groups of urease. To prepare an alkaline phosphatase-antibody conjugate, a one-step glutaraldehyde method is the simplest procedure (Voller et al., *Bull. W.H.O.*, 53:55–65 [1976]). This antibody-alkaline phosphatase conjugation protocol uses an enzyme immunoassay grade of the alkaline phosphatase enzyme.

The end product of an ELISA is a signal typically observed as the development of color or fluorescence.

Typically, this signal is read (i.e., quantitated) using a suitable spectrocolorimeter (i.e., a spectrophotometer) or spectrofluorometer. The amount of color or fluorescence is directly proportional to the amount of immobilized antigen. In some embodiments of the present invention, the amount of antigen in a sample (e.g., the amount of βA-MDA peptide in a blood or CSF sample) is quantitated by comparing results obtained for the sample with a series of control wells containing known concentrations of the antigen (i.e., a standard concentration curve). A negative control is also included in the assay system.

It is contemplated that any suitable chromogenic or fluorogenic substrates will find use with the enzyme-conjugated antibodies of the present invention. In some embodiments of the present invention, the substrate p-nitrophenyl phosphate (NPP) in diethanolamine is the preferred substrate for use in colorimetric ELISA methods, and 4-methylumbelliferyl phosphate (MUP) is the preferred alkaline phosphatase substrate in fluorometric ELISA methods.

The present invention provides various ELISA protocols for the detection and/or quantitation of βA-MDA antigen in a sample. In one embodiment, the present invention provides a "direct ELISA" for the detection of βA-MDA antigen in a sample. In some embodiments, the antigen of interest in a sample (i.e., the βA-MDA peptide) is bound (along with unrelated antigens) to the solid support (e.g., a microtiter plate well). The immobilized antigen is then directly detected by the antigen-specific enzyme-conjugated antibody, also provided by the present invention. Addition of an appropriate detection substrate results in color development or fluorescence that is proportional to the amount of antigen present in the well.

In another embodiment, the present invention provides an indirect ELISA for the detection of antigen in a sample. In this embodiment, antigen of interest in a sample is immobilized (along with unrelated antigens) to a solid support (e.g., a microtiter plate well) as in the direct ELISA, but is detected indirectly by first adding an antigen-specific antibody, then followed by the addition of a detection antibody specific for the antibody that specifically binds the antigen, also known as "species-specific" antibodies (e.g., a goat anti-rabbit antibody), which are available from various manufacturers known to one in the art (e.g., Santa Cruz Biotechnology; Zymed; and Pharmingen/Transduction Laboratories).

In some embodiments, the concentration of sample added to each well is titrated, so as to produce an antigen concentration curve. In other embodiments, the concentration of conjugated antibody is titrated. Indeed, such titrations are typically performed during the initial development of ELISA systems.

In another embodiment, the present invention provides "sandwich ELISA" methods, in which the antigen in a sample is immobilized on the solid support by a "capture antibody" that has been previously bound to the solid support. In general, the sandwich ELISA method is more sensitive than other configurations, and is capable of detecting 0.1–1.0 ng/ml protein antigen. As indicated above, the sandwich ELISA method involves pre-binding the "capture antibody" which recognizes the antigen of interest (i.e., the βA-MDA peptide) to the solid support (e.g., wells of the microtiter plate). In some embodiments, a biotinylated capture antibody is used in conjunction with avidin-coated wells. Test samples and controls are then added to the wells containing the capture antibody. If antigen is present in the samples and/or controls, it is bound by the capture antibody.

In some embodiments, after a washing step, detection of antigen that has been immobilized by the capture antibody is detected directly (i.e., a direct sandwich ELISA). In other embodiments detection of antigen that has been immobilized by the capture antibody is detected indirectly (i.e., an indirect sandwich ELISA). In the direct sandwich ELISA, the captured antigen is detected using an antigen-specific enzyme-conjugated antibody. In the indirect sandwich ELISA, the captured antigen is detected by using an antibody directed against the antigen, which is then detected by another enzyme-conjugated antibody which binds the antigen-specific antibody, thus forming an antibody-antigen-antibody-antibody complex. In both the direct and indirect sandwich ELISAs, addition of a suitable detection substrate results in color development or fluorescence that is proportional to the amount of antigen that is present in the well.

In the sandwich ELISA, the capture antibody used is typically different from the second antibody (the "detection antibody"). The choice of the capture antibody is empirical, as some pairwise combinations of capture antibody and detection antibody are more or less effective than other combinations. The same monoclonal antibody must not be used as both the capture antibody and the conjugated detection antibody, since recognition of a single epitope by the capture antibody will preclude the enzyme-conjugated detection antibody from binding to the antigen. However, in some embodiments, two different monoclonal antibodies that recognize different epitopes are used in this assay. In other embodiments, the same polyclonal antibody preparation is used as both the capture antibody and conjugated detection antibody, since multiple epitopes are recognized in the pool of polyclonal antibody species. In some embodiments, the polyclonal anti-βA-MDA antibody provided by the present invention is used as both the capture antibody and the enzyme-conjugated detection antibody in the sandwich ELISA. Alternatively, in other embodiments, it is contemplated that a monoclonal or polyclonal antibody which recognizes an unmodified βA peptide will find use as the capture antibody, and the anti-βA-MDA polyclonal antibody is used as the enzyme-conjugated detection antibody.

Antibodies which recognize unmodified forms of the βA peptide suitable for use in the present invention are readily available from various manufacturers, including Oncogene Research Products (Catalog Nos. PC149, PC150, PC151 and PC152), Santa Cruz Biotechnology (Catalog Nos. sc-5399, sc-5400, sc-7496, sc-7497, sc-7498 and sc-9129), Sigma (Catalog Nos. A5213), Zymed (Catalog Nos. 13-0100 and 71-5800) and Pharmingen/Transduction Laboratories (Catalog Nos. 66471G, 66481G and 66491G). However, it is not intended that the present invention be limited to the antibodies listed here, as other antibodies also find use with the present invention. It is also not intended that the sandwich ELISA of the present invention be limited to any particular sandwich ELISA method.

Furthermore, it is not intended that the present invention be limited to the direct ELISA and sandwich ELISA protocols particularly described herein, as the art knows well numerous alternative ELISA protocols that also find use in the present invention (See, e.g., Crowther, "Enzyme-Linked Immunosorbent Assay (ELISA)," in *Molecular Biomethods Handbook*, Rapley et al. [eds.], pp. 595–617, Humana Press, Inc., Totowa, N.J. [1998]; and Ausubel et al. (eds.), *Current Protocols in Molecular Biology*, Ch. 11, John Wiley & Sons, Inc., New York [1994]). Thus, any suitable ELISA method including, but not limited to, competitive ELISAs also find use with the present invention.

In another embodiment, the present invention provides methods for the detection and quantitation of βA-MDA reactive antibodies. Briefly, in some embodiments, variations of indirect ELISAs are used. In preferred embodiments, antigen (i.e., βA-MDA) is first used to coat the wells of a 96-well microtiter plate. The test sample is then added to the antigen-coated wells. If the test sample contains βA-MDA reactive antibodies, these antibodies specifically bind to the purified antigen coating the well. The βA-MDA reactive antibodies are then visualized by the addition of a second detection antibody, where the detection antibody is coupled to an enzyme and is species-specific or isotype-specific for anti-βA-MDA antibody. As with all ELISA methods, appropriate negative and positive controls are included in order to ensure the reliability of the assay results.

It is contemplated that patients with Alzheimer's disease produce βA-MDA-reactive auto-antibodies, and an ELISA to detect βA-MDA reactive antibodies in such samples will find use in the diagnosis of Alzheimer's disease. It is further contemplated that the presence of anti-βA-MDA auto-antibodies in a patient is diagnostic of Alzheimer's disease.

It is also contemplated that the present invention will find use in detection of βA-MDA reactive antibodies in various other settings (e.g., in the screening of monoclonal hybridoma culture supernatants [i.e., conditioned hybridoma culture medium], ascites fluid and/or polyclonal antisera).

The present invention also provides ELISA amplification systems. These embodiments produce at least 10-fold, and more preferably, a 500-fold increase in sensitivity over traditional alkaline phosphatase-based ELISAs. In one preferred embodiment of the ELISA amplification protocol, bound alkaline phosphatase acts on an NADPH substrate, whose reaction product initiates a secondary enzymatic reaction resulting in a colored product. Each reaction product from the first reaction initiates many cycles of the second reaction in order to amplify the signal (See e.g., Bio-Rad ELISA Amplification System, Cat. No. 19589-019).

The present invention also provides ELISA kits for the detection of antibodies and/or antigen. In addition, in some embodiments, the kits are customized for various applications. However, it is not intended that the kits of the present invention be limited to any particular format or design. In some embodiments, the kits of the present invention include, but are not limited to, materials for sample collection (e.g., spinal and/or venipuncture needles), tubes (e.g., sample collection tubes and reagent tubes), holders, trays, racks, dishes, plates (e.g., 96-well microtiter plates), instructions to the kit user, solutions or other chemical reagents, and samples to be used for standardization, and/or normalization, as well as positive and negative controls. In particularly preferred embodiments, reagents included in ELISA kits specifically intended for the detection of βA-MDA peptide or anti-βA-MDA antibodies include control βA-MDA peptide, anti-βA-MDA antibody, anti-βA-MDA antibody-enzyme conjugate, 96-well microtiter plates precoated with control βA-MDA peptide, suitable capture antibody, 96-well microtiter plates precoated with a suitable βA-MDA capture antibody, buffers (e.g., coating buffer, blocking buffer, and distilled water), enzyme reaction substrate and premixed enzyme substrate solutions.

It is contemplated that the compositions and methods of the present invention will find use in various settings, including research and clinical diagnostics. For example, the anti-βA-MDA antibody of the present invention also finds use in studies of APP metabolism and in in situ hybridization studies of brain tissue sections to observe Alzheimer's disease pathology. In addition, methods to quantitate βA-MDA in samples find use in monitoring and/or determining the effectiveness of Alzheimer's disease treatment, as it is contemplated that decreasing levels of βA-MDA peptide in a subject's samples over time indicates the effectiveness of an Alzheimer's disease treatment. Uses of the compositions and methods provided by the present invention encompass human and non-human subjects and samples from those subjects, and also encompass research as well as diagnostic applications. Thus, it is not intended that the present invention be limited to any particular subject and/or application setting.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); cm (centimeters); g (grams); l or L (liters); µg (micrograms); µl (microliters); µm (micrometers); µM (micromolar); µmol (micromoles); mg (milligrams); ml (milliliters); mm (millimeters); mM (millimolar); mmol (millimoles); M (molar); mol (moles); ng (nanograms); nm (nanometers); nmol (nanomoles); N (normal); pmol (picomoles); Aldrich (Sigma/Aldrich, Milwaukee, Wis.); Amersham (Amersham/Pharmacia Biotech, Piscataway, N.J.); Bio-Rad (Bio-Rad Laboratories, Hercules, Calif.), Boehringer Mannheim (Boehringer Mannheim Corporation, Indianapolis, Ind.); Dynex (Dynex Technologies, Inc., Chantilly, Va.); Fisher Scientific (Fisher Scientific, Pittsburgh, Pa.), GiboBRL/Life Technologies (GibcoBRL/Life Technologies, Gaithersburg, Md.), Oncogene Research Products (Oncogene Research Products, Cambridge, Mass.); Pharmingen/Transduction Laboratories (Pharmingen/Transduction Laboratories/Becton Dickinson Company, San Diego, Calif.); Pierce Chemical Company (Pierce Chemical Company, Rockford, Ill.); Promega (Promega Corporation, Madison, Wis.); Santa Cruz Biotechnology (Santa Cruz Biotechnology, Inc., Santa Cruz, Calif.); Sigma (Sigma Chemical Co., St. Louis, Mo.); and Zymed (Zymed Laboratories, Inc., South San Francisco, Calif.).

Brain tissue samples from an Alzheimer's disease patient and from a matched control individual (i.e., without Alzheimer's disease) were obtained from the Alzheimer's Disease Center at University of California, San Diego.

EXAMPLE 1

In Vitro Modification of Synthetic β-Amyloid Fragment 1–42

β-amyloid peptide fragment 1–42 (SEQ ID NO: 1; Sigma, Catalog No. A9810) was oxidatively modified to form a β-amyloid peptide containing malondialdehyde adduct(s). This modified peptide is herein called βA-MDA. A 100 µl volume of modification buffer (88 µl bis-dimethylacetal (Aldrich), 12 µl of 4 N HCl, 400 µl water, incubated at 37° C. for 30 minutes, pH to 7.4 with NaOH) was used to dissolve 1.0 mg of the unmodified β-amyloid peptide fragment. The resulting solution was incubated at 37° C. for 3 hours, followed by lyophilization to dryness. βA-MDA was then resuspended and stored at −70° C.

EXAMPLE 2

Generation and Purification of Polyclonal Anti-βA-MDA Antibodies

Antisera against the βA-MDA peptide was raised in rabbits using standard techniques. Briefly, the βA-MDA peptide was conjugated to keyhole limpet hemocyanin (KLH), mixed with an equal volume of Freund's incomplete adjuvant, and used to immunize New Zealand white rabbits by injection at 8–10 subcutaneous dorsal sites. Animals received inoculation boosts at weeks 4, 6 and 8. Bleeds were obtained and tested at weeks 8, 12 and 16 for analysis. When antibody levels plateaued, the rabbits were exsanguinated by cardiac puncture, and the collected sera was stored at −80° C. until used.

Antibodies contained within the anti-βA-MDA antisera were purified by ammonium sulfate precipitation and immunoaffinity purification using standard techniques. Briefly, the anti-βA-MDA antiserum was subjected to ammonium sulfate precipitation by the addition of ammonium sulfate to 50% saturation. At this concentration, the IgG fraction was precipitated, while a significant percentage of the contaminating proteins remained in solution. The resulting precipitate was pelleted by centrifugation and washed once in 50% saturated ammonium sulfate solution. The precipitate was pelleted again, then resuspended and dissolved in PBS. The solution was then dialyzed once against PBS.

The PBS solution containing the precipitated IgG fraction was further purified using affinity chromatography. The affinity resin used in this purification was an activated CH-Sepharose coupled to βA-MDA peptide prepared as described in Example 1, at a concentration of 10 mg of peptide per 1.0 g of sepharose. The IgG fraction was loaded onto the column and washed with 6 volumes of PBS, followed by a second wash with 6 volumes of PBS containing 1.0 M NaCl. The PBS solution containing the precipitated IgG was loaded onto the column, washed, and the anti-βA-MDA-specific IgG fraction was eluted in 2.0 ml fractions with 100 mM glycine, pH 2.5. Following elution, 200 μl of 1.0 M Tris pH 8.1 was added to the fractions. The concentration of the immunoglobulin was determined using a total protein colorimetric determination (Bio-Rad).

It is not intended that the present invention be limited to the use of this particular protocol for the production and purification of antibodies, as numerous protocols are available and known to those in the art (See, e.g., Sambrook et al. (eds.), Molecular Cloning, Cold Spring Harbor Laboratory Press [1989]; Harlow and Lane (eds.), *Antibodies: A Laboratory Manual*, Cold Spring Harbor Laboratory Press [1988]; and Ausubel et al. (eds.), *Current Protocols in Molecular Biology*, Ch. 11, John Wiley & Sons, Inc., New York [1994]). The only criterion for antibody production methods finding use with the invention is that sufficiently purified antibody preparations be produced. As discussed further in Example 3, any method suitable for the production of monoclonal antibodies also finds use with the present invention.

EXAMPLE 3

Generation of Monoclonal Anti-βA-MDA Antibodies

For preparation of monoclonal antibodies directed toward βA-MDA, any technique that provides for the production of monoclonal antibodies will find use with the present invention. This Example provides but one method for the production of such monoclonal antibodies. However, it is not intended that the present invention be limited to this particular method, as any method suitable for the production of anti-βA-MDA peptide antibodies will find use with the present invention.

A) Inoculation and Recovery of Antibody-Producing Cells

The modified βA-MDA peptide fragment, or a portion thereof, is administered as an antigen to a suitable animal (e.g., rat, mouse or rabbit). The dosage of the antigen administered per animal is typically be between 0.1 and 10 mg when no adjuvant is used, and between 1.0 and 100 μg when an adjuvant is used. As an adjuvant, Freund's complete adjuvant (FCA), Freund's incomplete adjuvant (FIA), aluminum hydroxide adjuvant or the like are suitable for use. Immunization is by any suitable route and immunization schedule, as known to those in the art. Subsequently, at 1 to 10 days, preferably 3 days, after the final immunization, antibody-producing cells (e.g., spleen, lymph nodes and peripheral blood cells) are collected.

B) Cell Fusion and Formation of Hybridoma Cell Lines

In order to obtain hybridomas which produce the monoclonal antibody, cell fusions between the antibody-producing cells described above and myeloma cells are performed. In particularly preferred embodiments, spleen cells harvested from the animals immunized as described above are used. The fusion partner chosen for production of the monoclonal antibodies is preferably a cell line which has drug selectivity and cannot survive in HAT selective medium (i.e., containing hypoxanthine, aminopterin and thymidine) unless fused to antibody-producing cells. Mouse myeloma cell lines including but not limited to, P3X63Ag.8.U1(P3U1), Sp2/0, NS-1 and other cell lines find use as suitable myeloma cell lines for fusion with antibody-producing cells.

The myeloma cells and the antibody-producing cells described above are fused using any suitable method. For example, $1 \times 10_9$ cells/ml of the antibody-producing cells and $1 \times 10_8$ cells/ml of the myeloma cells are mixed together in equal volumes in an animal cell culture medium such as serum-free DMEM or RPMI-1640, and reacted in the presence of a cell fusion promoting agent. In some embodiments, polyethylene glycol with an average molecular weight of 1,500 Da is used as the cell fusion promoting agent. Alternatively, the antibody-producing cells and the myeloma cells are fused in a commercial cell fusion apparatus utilizing electric stimulation (e.g., electroporation). These cells are plated in appropriate vessels and incubated under suitable conditions, as described below.

C) Selection and Cloning of Hybridoma Lines

Following cell fusion, suitable hybridomas are selected from the cell cultures. As a method for this selection, the resultant cell suspension is appropriately diluted with fetal bovine serum containing RPMI-1640 medium or the like, and then plated on microtiter plates at a density of about $2 \times 10_5$ cells/well. A selective medium is added to each well, and the cells are cultured in that selective medium. As a result, about 14 days after the start of cultivation in the selective medium, the growing cells develop into antibody-producing hybridomas.

Subsequently, screening is performed in order to determine the presence of the antibody of interest in the culture supernatant of the hybridomas. Hybridoma screening is performed using any suitable methods. For example, a part of the culture supernatant of a well in which a hybridoma is grown is collected and subjected to enzyme immunoassay or radioimmunoassay, as described herein.

The fused cell preparations are cloned using a suitable method (e.g., the limiting dilution method or the like). Finally, the monoclonal antibody-producing hybridoma is established and maintained. In preferred embodiments, aliquots of the monoclonal antibody producing hybridoma are frozen and retained as stock cultures.

D) Recovery and Purification of the Monoclonal Antibody

In some embodiments of the present invention, conventional cell culture methods or the abdominal dropsy formation method are employed for recovering the monoclonal antibody from the a monoclonal antibody-producing hybridomas.

In the cell culture method, the hybridoma is cultured in an animal cell culture medium such as 10% fetal bovine serum-containing RPMI-1640 medium, MEM medium or a serum-free medium under conventional culture conditions (e.g., at 37° C. under 5% $CO_2$) for 2 to 10 days. Then, the monoclonal antibody is then harvested from the culture supernatant, using methods known to those in the art.

In the abdominal dropsy formation method, about $1 \times 10_7$ cells of the hybridoma are administered into the abdominal cavity of an animal syngeneic to the mammal from which the myeloma cells were derived, to thereby greatly propagate the hybridoma. One to two weeks thereafter, the abdominal dropsy or serum is collected.

The antibody obtained is then purified as necessary, using methods known in the art (e.g., protein A/protein G affinity, ammonium sulfate salting out, ion exchange chromatography, gel filtration, affinity chromatography, or using these methods in combination).

The antibodies produced by this method find use in numerous applications, including Western immunoblotting, enzyme linked immunosorbent assays (ELISAs), immunoprecipation, immunoaffinity purification, and immunohistochemistry.

EXAMPLE 4

Western Immunoblotting Using βA Peptides

βA and βA-MDA peptides were analyzed by Western immunoblotting to determine the reactivity and specificity of the polyclonal anti-βA-MDA antibody produced according to the method described in Example 2. This method utilized a chemiluminescence detection protocol (ECL, Amersham) that was performed according to the manufacturer's instructions. The secondary antibody used for visualization was a goat anti-rabbit IgG-horseradish peroxidase (HRPO)-conjugated antibody (Santa Cruz).

Briefly, the protein concentrations of the synthetic βA peptide fragment 1–42 and the modified βA-MDA peptide (described in Example 1) were determined by a Bradford-based protein assay (Bio-Rad). Following protein quantitation, 1.0 μg samples of each protein were boiled for 5 minutes in Laemmli buffer. Samples were then resolved using SDS-PAGE containing 20% polyacrylamide and electroblotted onto nitrocellulose. Blots were incubated overnight in blocking buffer (phosphate buffered saline [PBS] containing 5% (w/v) nonfat dry milk and 0.1% Tween-20), then incubated for 2 hours with the polyclonal anti-βA-MDA antibody at a 1:1,000 dilution in blocking buffer. Membranes were washed 3 times in washing buffer (PBS containing 0.1% Tween-20) for 15 minutes each wash, then incubated for 1 hour with horseradish peroxidase-conjugated goat anti-rabbit IgG (Santa Cruz) diluted 1:5,000 in blocking buffer, then again washed again 3 times in washing buffer for 15 minutes each wash. Membranes were then incubated in chemiluminescent detection substrate (ECL, Amersham) for 1 minute and signal was detected on X-ray film.

The results indicated that the anti-βA-MDA antibody detected the βA-MDA synthetic peptide, but not an unmodified βA peptide. In addition, the preimmune control serum showed no reactivity towards either the βA-MDA peptide nor the unmodified βA peptide.

EXAMPLE 5

Immunoprecipitation of βA from Brain Tissue

Following the determination of the specificity of the purified anti-βA-MDA antibody as described in Example 4, the antibody was tested in experiments to determine whether it was capable of detecting proteins in human brain cortex tissue from an Alzheimer's disease patient and a matched control individual. Post-mortem brain tissue obtained from an Alzheimer's disease patient and a matched control individual was first subjected to immunoprecipitation using a commercially available anti-βA antibody. Western blots were used to analyze these immunoprecipitates, as described in Example 6.

Briefly, 100 mg of brain homogenate were combined with 3.0 ml of ice cold RIPA buffer (PBS containing 1% Nonidet P-40 [NP-40], 0.5% sodium deoxycholate, 0.1% SDS, 0.1 mg/ml phenyl methanesulfonyl fluoride [PMSF], and 0.3 trypsin inhibitor units [TIU] aprotinin) and incubated at 4° C. for 10 minutes. This mixture was centrifuged at 1,000×g for 10 minutes at 4° C. The supernatant was transferred to a fresh 15 ml conical centrifuge tube on ice. The lysate was precleared by adding 1.0 μg of control rabbit IgG (Sigma) together with 20 μl of suspended Protein A-Agarose beads (Santa Cruz Biotechnologies). This mixture was incubated at 4° C. for 30 minutes.

The Protein A-agarose beads were pelleted by centrifugation at 1,000×g for 5 minutes at 4° C., and the supernatant was removed and placed in a fresh 15 ml conical centrifuge tube on ice. Following protein quantitation (Protein Microassay, Bio-Rad), 500 μg of this total cellular protein supernatant was transferred to a 1.5 ml microcentrifuge tube, to which was added 2 μg of a commercial anti-βA antibody (Transduction Laboratories, Affinity Research Products Catalog No. AK6905). This mixture was incubated for 1 hour at 4° C. After this time, 20 μl of suspended Protein A-agarose beads were added to the eppendorf tube, the tube was capped, and incubated at 4° C. on either a rocker platform or tube rotating device overnight.

Following this overnight incubation, the Protein A-agarose beads were pelleted by centrifugation at 1,000×g for 5 minutes at 4° C., and the supernatant was aspirated and discarded. The resulting pellet was washed 4 times with 1 ml RIPA buffer, followed each time by recentrifugation. After the final wash, the supernatant was aspirated and discarded, and the pellet was resuspended in 40 μl of Laemmli buffer.

EXAMPLE 6

Western Immunoblotting Analysis of Human Brain Tissue Immunoprecipitates Using Anti-βA-MDA Antibody Brain tissue anti-βA-MDA immunoprecipitates (prepared as described in Example 5) were analyzed in a Western blot using the protocol provided in Example 4. Briefly, the brain tissue immunoprecipitates resuspended in 40 μl of Laemmli buffer were boiled for 2–3 minutes, and 20 μl aliquots were loaded and resolved on 20% polyacrylamide SDS-PAGE. Unused samples were stored at −20° C.

Following electrophoresis, samples were electroblotted onto nitrocellulose. Blots were incubated overnight in blocking buffer (phosphate buffered saline [PBS] containing 5% (w/v) nonfat dry milk and 0.1% Tween-20), then incubated for 2 hours with the polyclonal anti-βA-MDA antibody (prepared as described in Example 2) at a 1:1,000 dilution in blocking buffer. Membranes were washed 3 times in washing buffer (PBS containing 0.1% Tween-20) for 15 minutes each wash, then incubated for 1 hour with horseradish peroxidase-conjugated goat anti-rabbit IgG (Santa Cruz) diluted 1:5,000 in blocking buffer, then again washed again 3 times in washing buffer for 15 minutes each wash. Membranes were then incubated in chemiluminescent detection substrate (ECL, Amersham) for 1 minute and luminescence signal was detected on X-ray film.

As shown in FIG. 1, this Western blot demonstrates that the anti-βA-MDA antibodies detect at least one and possibly multiple proteins in the immunoprecipitate from the brain of an Alzheimer's disease patient (lane indicated as "AD"). However, no proteins were detected in the brain tissue immunoprecipitate from a disease-free control individual (lane indicated as "CONTROL").

The specificity of the primary and secondary antibodies were further confirmed by an anti-β-galactosidase antibody immunoprecipitation of brain tissue from an Alzheimer's disease patient. The immunoprecipitation protocol used was identical to that described in Example 5. This anti-β-galactosidase immunoprecipitate was blotted and probed in parallel with the other two samples in FIG. 1 using the same anti-βA-MDA primary antibody and the HRPO-conjugated secondary antibody (lane indicated as "β-GAL"). As shown in the Figure, the anti-βA-MDA primary antibody showed no reactivity towards the anti-β-galactosidase immunoprecipitate from the brain tissue of the Alzheimer's patient.

Thus, the anti-βA-MDA polyclonal antibody produced as described in Example 2 recognizes at least one modified endogenous βA-MDA species present in the brain tissue of individuals with Alzheimer's disease, but not in the brain tissue of unaffected individuals.

EXAMPLE 7

Covalent Conjugation of Antibody and Reporter Enzyme

This Example describes the preparation of an antibody-enzyme conjugate for use in immunoassay (e.g., ELISA) methods for detection of Alzheimer's disease. Conjugation of enzymes to antibodies involves the formation of a stable, covalent linkage between an enzyme (e.g., HRPO or alkaline phosphatase) and the antibody (e.g., the polyclonal anti-βA-MDA antibody, or an antibody which recognizes the anti-βA-MDA antibody), where neither the antigen-binding site of the antibody nor the active site of the enzyme is functionally altered. It is not intended that the present invention be limited to the antibody-enzyme conjugation method provided herein, as other methods also find use with the present invention, as known to one skilled in the art.

A detailed method for the synthesis of an HRPO-conjugated antibody of the present invention is provided herein. A purified antibody (e.g., a polyclonal or monoclonal anti-βA-MDA antibody) solution is dialyzed against 100 mM phosphate buffer (50 mM $NaH_2PO_4$, 50 mM $Na_2HPO_4$, pH 6.8) overnight at 4° C., at an antibody concentration of at least 1.0 mg/ml. A 10 mg/ml solution of HRPO enzyme (Type VI, Sigma No. P8375) is prepared in carbonate buffer (1.36 g sodium carbonate, 7.35 g sodium bicarbonate in 1.0 liter water, pH to 9.2). Then, 250 μl of $NaIO_4$ solution (1.71 mg $NaIO_4$/ml water, made fresh) and 250 μl of HRPO/carbonate solution are mixed together and incubated at room temperature for 2 hours in the dark.

Then, 1.0 ml of the dialyzed 1 mg/ml antibody solution and 0.5 ml of the HRPO/carbonate/$NaIO_4$ solution are placed in a plugged glass wool column, 250 mg Sephadex G-25 is added to this mixture, and incubated for 3 hours at room temperature in the dark.

The antibody-enzyme conjugate is eluted from the column by washing with 750 μl carbonate buffer. To this eluate, 38 μl of $NaBH_4$ solution (0.1 mM NaOH containing 5 mg/ml $NaBH_4$, made fresh) is added, and the mixture is incubated for 30 minutes at room temperature in the dark. After this 30 minute incubation, an additional 112 μl of $NaBH_4$ solution is added, and the mixture is incubated for 60 minutes at room temperature in the dark.

After this incubation, 900 μl of saturated $(NH_4)_2SO_4$ solution is added, and the mixture is incubated at 4° C. for 30 minutes, followed by centrifugation at 10,000×g at 4° C. for 15 minutes. The supernatant is discarded, and the pellet is resuspended in 750 μl of TEN buffer (40 mM Tris, 1 mM EDTA, 150 mM NaCl, pH 7.2).

The resuspended pellet is dialyzed against TEN buffer overnight at 4° C. The next day, the antibody-enzyme conjugate is removed, and bovine serum albumin (BSA) added to a final concentration of 20 mg/ml BSA. For storage of the antibody-enzyme conjugate, an equal volume of glycerol is added, and the mixture is placed at −20° C.

EXAMPLE 8

Enzyme-Linked Immunosorbent Assay (ELISA)

This Example describes experiments useful for the detection and/or quantitation of the levels of βA-MDA peptide in various samples (e.g., samples obtained from patients, as well as research samples). In these experiments, the anti-βA-MDA antibody (prepared as described in Example 2) is used.

A. Direct ELISA Method

As discussed previously, in some embodiments, the direct ELISA method typically involves binding an antigen (e.g., the βA-MDA peptide) directly to microtiter wells, binding of an antigen-specific antibody-enzyme conjugate to the immobilized antigen, followed by detection of that antibody-enzyme conjugate by either colorimetric or fluorometric detection of the enzyme reaction product. Numerous variations of the direct ELISA protocol are known in the art. This Example provides one protocol suitable for use in the present invention.

Briefly, positive control antigen, a negative control antigen, and experimental samples are diluted in coating buffer (64 mM $Na_2CO_3$, 136 mM $NaHCO_3$, pH 9.6) to a concentration of ≦10 μg/ml. In experiments utilizing a pure antigen solution for the coating step, the concentration used is <2 μg/ml. However, in preferred embodiments, a single optimum concentration, or range of concentrations, of the positive control antigen is determined empirically. First, 50 μl of coating buffer is added to the wells of a suitable 96-well polyvinyl or polystyrene microtiter plate (e.g., Immulon 2™ or Immulon 4™ microtiter plates, Dynex Technologies, Catalog Nos. 011-010-3450 and 011-010-3850, respectively) and tapped to ensure that the solution is evenly distributed in the well. Then, 100 μl of positive control antigen, negative control antigen or experimental sample are added to the appropriate wells. Serial dilutions of the control antigens and/or experimental samples are then made within the rows of the plate. For each sample, 8–10 two-fold or three-fold serial dilutions are made, in order to ensure that at least one of the subsequent absorbance values is within the linear range of the assay. A standard dilution series for the control antigen ranges from 0.1 to 1000 ng/ml. Duplicate or triplicate 96-well plates are used in order to ensure reproducibility. The plates are covered and incubated overnight at room temperature or for 2 hours at 37° C.

Following incubation, the antigen solutions in the microtiter plate wells are decanted, and the wells are rinsed three times with distilled water. Then, 200 µl of blocking buffer (phosphate buffered saline [PBS] containing 1 mM EDTA, 0.05% (w/v) Tween-20, 0.25% (v/v) bovine serum albumin [BSA], and 0.05% (w/v) sodium azide [NaN$_3$]) are added to each well. However, in experiments utilizing an HRPO-conjugated antibody in the ELISA detection step, sodium azide is not used in this or any subsequent buffer. The plates containing blocking buffer are incubated at room temperature for 30–60 minutes. The blocking buffer is decanted, and 50 µl of fresh blocking buffer is added to each well. Then, 100 µl of diluted antibody-enzyme conjugate (diluted in blocking buffer) is added to each well. An appropriate dilution of the antibody-enzyme conjugate must be empirically determined, however, a dilution 1:100 is commonly used, resulting in a concentration of antibody-enzyme conjugate between 25–400 ng/ml. However, in some embodiments, other concentrations are used. The plates are covered and incubated under conditions determined to be optimal for the test system (e.g., 30–60 minutes at 37° C.).

Following the incubation, the wells are decanted, then washed three times with distilled water. Each well is then filled with blocking buffer, incubated for 10 minutes at room temperature, then washed 3 more times with distilled water. The wells are then decanted, inverted and patted dry.

Following the wash steps, 50–75 µl of the appropriate enzyme substrate (in blocking buffer) are added to each well on the plate and incubated for approximately 1 hour at room temperature. When using alkaline phosphatase systems, either 4-methylumbelliferyl phosphate (MUP) or p-nitrophenyl phosphate (NPP) substrate solutions are used to achieve either fluorescence or color development, respectively (MUP substrate solution: 0.2 mM MUP [Sigma Catalog No. M8883], 50 mM Na$_2$CO$_3$, 0.05 mM MgCl$_2$, store at room temperature; NPP substrate solution: 3 mM NPP [Sigma Catalog No. 104-0], 50 mM N % CO$_3$, 0.05 M MgCl$_2$, store at 4° C.). Premade substrate solutions are commercially available (e.g., Bio-Rad ELISA Soluble Substrate Systems, Catalog Nos. 172-1063, 1064, 1066, 1067 and 1068). To assay low levels of enzyme activity, the plate is incubated for several hours with the appropriate substrate solution. The enzymatic reactions on the plate are stopped by adding 25 µl of 500 mM NaOH to the wells.

The enzymatic reaction in each well is monitored and/or quantitated visually or in an appropriate microtiter plate reader (e.g., Bio-Rad Benchmark Microplate Reader, Catalog No. 170–6850). For example, hydrolysis of the NPP substrate by alkaline phosphatase results in the appearance of a yellow reaction product, which is monitored by absorbance at a 405 nm wavelength. Hydrolysis of the MUP substrate results in visible illumination with use of a long wavelength UV lamp, and is quantitated in a microtiter plate spectrofluorometer using a 365 nm wavelength excitation filter and a 450 nm wavelength emission filter (See, e.g., Dynex Technologies, MFX™ Microplate Fluorometer). The absorbance versus the known antigen concentrations are plotted, and a standard curve that reads within the linear range of the spectrophotometer or spectrofluorometer is prepared. To determine the antigen concentration of the experimental samples, the absorbance of the experimental samples is compared to the absorbance values of the standard curve.

In view of numerous alternative protocols for a direct ELISA known in the art, it is not intended that the direct ELISA of the present invention be limited to this or any particular direct ELISA method.

B. Sandwich ELISA Method

In one embodiment of the present invention, the sandwich ELISA method involves first binding a "capture antibody" which recognizes the antigen of interest (i.e., the βA-MDA peptide) to the wells of a microtiter plate. Samples containing control concentrations of antigen or experimental samples are then added to the wells containing antibody, where the antigen binds to the antibody present in the wells. After a washing step, a second antibody specific for the antigen and containing a conjugated enzyme is added to the wells, where it specifically binds the bound antigen. After a washing step, the amount of second antibody, and thus the amount of antigen in the well, is quantitated by measuring activity of the conjugated enzyme. As in the direct ELISA, the amount of antigen in an experimental sample (e.g., the amount of βA-MDA peptide in a blood or CSF sample) is proportional to the color or fluorescence intensity in the well, and is quantitated by comparing the color or fluorescence value to the values for known concentrations of the antigen in the same assay (i.e., a standard concentration curve).

The anti-βA-MDA antibody (e.g., the antibody produced according to Example 2) is suitable for use as both the capture antibody, as well as the conjugated detection antibody. However, commercially available antibodies (including, for example, antibodies from Oncogene Research Products [Catalog numbers PC149, PC150, PC151 and PC152], Santa Cruz Biotechnology [Catalog numbers sc-5399, sc-5400, sc-7496, sc-7497, sc-7498 and sc-9129], Sigma [Catalog number A5213], Zymed [Catalog numbers 13-0100 and 71-5800] and Pharmingen [Catalog numbers 66471G, 66481G and 66491G]) capable of recognizing the unmodified form of the βA peptide are also suitable for use as the capture antibody.

A sandwich ELISA protocol suitable for use with the present invention is provided below. A purified βA-specific antibody (the "capture antibody") is diluted to a concentration of 0.2 to 10 µg/ml in PBSN (PBS containing 0.05% sodium azide [NaN$_3$]). However, in experiments using HRPO-conjugated antibody, sodium azide is not used in this or any subsequent steps. The wells of a 96-well microtiter plate are coated with the capture antibody by dispensing 50 µl aliquots of the antibody to the wells. Simultaneously, duplicate or triplicate plates are made and analyzed in parallel to ensure reproducibility. The plate is tapped or shaken to ensure that the antibody solution is evenly distributed over the bottom of each well. The plates are covered and incubated overnight at room temperature or for 2 hours at 37° C.

Following incubation, the antibody-containing solution in the plate wells is decanted. The wells are rinsed a total of three times with distilled water. After washing, each well is filled with blocking buffer (PBS containing 0.05% (w/v) Tween-20, 0.25% (w/v) bovine serum albumin [BSA], 1 mM EDTA and 0.05% (w/v) sodium azide [NaN$_3$]) and incubated for 30 minutes at room temperature. Following the incubation, the plate is rinsed with water three times, inverted, shaken and patted dry.

Following the blocking step, a serial dilution of purified antigen (e.g., the βA-MDA peptide) is made by successive three-fold dilutions in blocking buffer, resulting in a range of antigen concentrations (e.g., from 0.1 to 1000 ng/ml). Serial dilutions of the test samples are also made using blocking buffer. Ideally, dilutions of the experimental samples result in the samples containing between 1 and 100 ng/ml of specific antigen. Then, 50 µl aliquots of the standard antigen dilutions and the diluted experimental samples are placed in the wells of the 96-well microtiter plate, and incubated for at least two hours at room temperature. An antigen serving as a negative control (e.g., an unmodified βA peptide) is also be included.

Following incubation, the plate is rinsed three times with distilled water, and each well is then filled with blocking buffer and incubated for 10 minutes at room temperature.

The plate is then rinsed again three times in water, inverted, shaken and patted dry.

Then, 50 µl of specific antibody-enzyme conjugate are added to each well and incubated for 2 hours at room temperature. Reagents and methods for the detection and quantitation of the enzymatic reaction products are identical to those described in the direct ELISA.

Numerous variations of this sandwich ELISA protocol are suitable for use in the present invention. It is not intended that the sandwich ELISA of the present invention be limited to this or any particular sandwich ELISA method.

EXAMPLE 9

Analysis of βA-MDA from Blood and Cerebrospinal Fluid

As discussed above, endogenous unmodified βA is found in blood and cerebrospinal fluid (CSF). This Example describes methods to detect βA-MDA in the blood, serous fluid and CSF of a subject. The quantity of βA-MDA present in the samples is indicative of the severity of Alzheimer's disease, and is predictive for disease outcome (prognosis). In addition, by periodically testing the level of βA-MDA in the blood, serous fluid or CSF of a patient being treated for Alzheimer's disease, the efficacy of a particular treatment regime is monitored.

Blood samples (approximately 0.1 ml) are collected in standard clinical collection tubes containing an anticoagulant, such as heparin or EDTA. Blood plasma is separated by centrifugation at 1,000×g for 10 minutes at 4° C. within 30 minutes following sample collection. The blood and blood plasma samples are typically stored at 4° C. CSF is collected using standard procedures. CSF samples (approximately 0.1 ml) are typically stored at 4° C. These samples are then tested using the methods described herein (e.g., by Western blot [Example 4] and/or by ELISA [Example 8]).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in immunology, cell biology, neuroscience, medicine, chemistry, and molecular biology or related fields are intended to be within the scope of the following claims.

---

---

What is claimed is:

1. A method for detecting at least one antibody directed against a modified β-amyloid peptide comprising at least one malondialdehyde adduct, comprising:
    a) providing;
       i) a sample suspected of containing at least one antibody directed against a modified β-amyloid peptide comprising at least one malondialdehyde adduct, and
       ii) an isolated and modified β-amyloid peptide comprising at least one malondialdehyde adduct, and
       iii) a detection antibody;
    b) contacting said sample with said modified β-amyloid peptide, under conditions such that said antibody directed against a modified β-amyloid peptide comprising at least one malondialdehyde adduct binds to said modified β-amyloid peptide to form an antigen-antibody complex;
    c) contacting said antigen-antibody complex with said detection antibody, under conditions such that said detection antibody binds to said complex; and
    d) detecting said binding of said detection antibody to said antigen-antibody complex.

2. The method of claim 1, wherein said sample is selected from the group of samples consisting of blood, serous fluid, plasma, serum, cerebrospinal fluid, hybridoma conditioned culture medium, ascites fluid, and polyclonal antiserum.

3. The method of claim 1, wherein said sample is from a subject.

4. The method of claim 3, wherein said subject is human.

5. The method of claim 3, wherein said subject is selected from the group consisting of subjects displaying pathology resulting from Alzheimer's disease, subjects suspected of displaying pathology resulting from Alzheimer's disease, and subjects at risk of displaying pathology resulting from Alzheimer's disease.

6. The method of claim 1, wherein said method comprises a enzyme-linked immunosorbent assay.

7. The method of claim 6, wherein said enzyme-linked immunosorbent assay is selected from the group consisting of direct enzyme-linked immunosorbent assays, indirect enzyme-linked immunosorbent assays, direct sandwich enzyme-linked immunosorbent assays, indirect sandwich enzyme-linked immunosorbent assays, and competitive enzyme-linked immunosorbent assays.

8. The method of claim 1, wherein said detection antibody further comprises a conjugated enzyme, wherein said conjugated enzyme is selected from the group of enzymes consisting of horseradish peroxidases, alkaline phosphatases, ureases, glucoamylases, and β-galactosidases.

9. The method of claim 6, wherein said enzyme-linked immunosorbent assay further comprises an alkaline phosphatase amplification system.

10. The method of claim 1, wherein said modified β-amyloid peptide comprises the amino sequence of SEQ ID NO:1.

11. The method of claim 1, wherein said at least one malondialdehyde adduct comprises at least one malondialdehyde lysine adduct.

* * * * *